(12) United States Patent
Bennani et al.

(10) Patent No.: US 7,981,896 B2
(45) Date of Patent: Jul. 19, 2011

(54) PYRAZOLES FOR THE TREATMENT OF OBESITY AND OTHER CNS DISORDERS

(75) Inventors: Youssef L. Bennani, Boston, MA (US); Michael G. Campbell, Thunder Bay (CA); David Dastrup, Orem, UT (US); Emilie Porter Huck, Sudbury, MA (US)

(73) Assignee: Athersys, Inc., Cleveland, OH (US)

( * ) Notice: Subject to any disclaimer, the term of this patent is extended or adjusted under 35 U.S.C. 154(b) by 0 days.

(21) Appl. No.: 13/006,161

(22) Filed: Jan. 13, 2011

(65) Prior Publication Data

US 2011/0112088 A1    May 12, 2011

Related U.S. Application Data

(63) Continuation of application No. 11/699,662, filed on Jan. 30, 2007, now Pat. No. 7,897,634.

(60) Provisional application No. 60/771,768, filed on Feb. 9, 2006.

(51) Int. Cl.
*A61K 31/496* (2006.01)
*C07D 403/10* (2006.01)

(52) U.S. Cl. .................. 514/254.05; 544/371
(58) Field of Classification Search ............ 514/254.05; 544/371
See application file for complete search history.

(56) References Cited

U.S. PATENT DOCUMENTS

| 3,940,418 | A | 2/1976 | Hamilton |
| 6,660,744 | B1 * | 12/2003 | Hirst et al. ................. 514/262.1 |
| 2005/0080087 | A1 | 4/2005 | Pendri et al. |
| 2005/0256180 | A1 | 11/2005 | Bergmanis et al. |

FOREIGN PATENT DOCUMENTS

| EP | 0 647 629 | 10/1994 |
| WO | WO 2005/016877 | 2/2005 |
| WO | WO 2005/110994 | 11/2005 |
| WO | WO 2006/004937 | 1/2006 |

* cited by examiner

*Primary Examiner* — Joseph Kosack
*Assistant Examiner* — Matthew Coughlin
(74) *Attorney, Agent, or Firm* — Wood, Phillips, Katz, Clark & Mortimer

(57) ABSTRACT

This invention relates to compounds of the formula:

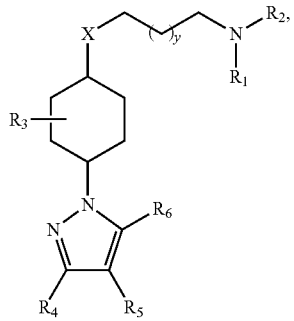

to compositions containing these compounds, and to methods of treatment employing the compounds and compositions.

4 Claims, No Drawings

US 7,981,896 B2

PYRAZOLES FOR THE TREATMENT OF OBESITY AND OTHER CNS DISORDERS

CROSS REFERENCE TO RELATED APPLICATIONS

This is application is a continuation application of the U.S. non-provisional application Ser. No. 11/699,662 filed Jan. 30, 2007 now U.S. Pat. No. 7,897,634, which claims the priority of U.S. Provisional Patent Application No. 60/771,768 filed on Feb. 9, 2006.

TECHNICAL FIELD

This invention relates to compounds having pharmacological activity, to compositions containing these compounds, and to a method of treatment employing the compounds and compositions. More particularly, this invention concerns certain pyrazole derivatives and their salts and solvates. These compounds alter $H_3$ histamine receptor activity. This invention also relates to pharmaceutical compositions containing these compounds and to a method of treating disorders in which histamine $H_3$ receptor modulation is beneficial.

BACKGROUND OF THE INVENTION

Histamine is a chemical messenger involved in various complex biological actions. When released, histamine interacts with specific macromolecular receptors on the cell surface or within a target cell to elicit changes in many different bodily functions. Various cell types including smooth muscle, blood cells, cells of the immune system, endocrine and exocrine cells as well as neurons respond to histamine by modulating the formation of intracellular signals, including of phosphatidylinositol, or adenylate cyclase. Evidence that histamine plays a role as a neurotransmitter was established by the mid-to-late 1970's (Schwartz, 1975) *Life Sci.* 17:503-518. Immunohistochemical studies identified histaminergic cell bodies in the tuberomammillary nucleus of the posterior hypothalamus with widespread projections in the dicencephalon and telencephalon (Inagaki et al., 1998) *J. Comp. Neurol.* 273:283-300.

Two histamine receptors ($H_1$ and $H_2$) were reported to mediate the biochemical actions of histamine on neurons. More recently, studies have demonstrated the existence of a third subtype of histamine receptor, the histamine $H_3$ receptor (Schwartz et al., 1986) *TIPS* 8: 24-28. Various studies have now demonstrated that histamine $H_3$ receptors are found on the histaminergic nerve terminals in the brains of several species, including man (Arrang et al., 1983) *Nature* 302: 832-837. The $H_3$ receptor found on the histaminergic nerve terminal was defined as an autoreceptor and could intimately control the amount of histamine released from the neurons. Histamine, the natural compound, was capable of stimulating this autoreceptor but testing of known $H_1$ and $H_2$ receptor agonists and antagonists suggested that the $H_3$ receptor has a distinct pharmacological profile. Further, $H_3$ receptors have been identified on cholinergic, serotonergic, glutamatergic and monoamine nerve terminals in the peripheral nervous system (PNS) and central nervous system including the cerebral cortex and cerebral vessels. These observations suggest that $H_3$ receptors are uniquely located to modulate histamine as well as other neurotransmitter release, and compounds that bind $H_3$ receptors could be important mediators of neuronal activity.

As stated, CNS histaminergic cell bodies are found in the magnocellular nuclei of the hypothalamic mammillary region and these neurons project diffusely to large areas of the forebrain. The presence of histaminergic cell bodies in the tuberomammillary nucleus of the posterior hypothalamus, a brain area involved in the maintenance of wakefulness, and their projections to the cerebral cortex suggest a role in modulating the arousal state or sleep-wake cycle. The histaminergic projection to many limbic structures such as the hippocampal formation and the amygdaloid complex suggest roles in functions such as autonomic regulation, control of emotions and motivated behaviors, and memory processes.

The concept that histamine is important for the state of arousal, as suggested by the location of histaminergic pathways, is supported by other types of evidence. Lesions of the posterior hypothalamus are well known to produce sleep. Neurochemical and electrophysiological studies have also indicated that the activity of histaminergic neurons is maximal during periods of wakefulness and is suppressed by barbiturates and other hypnotics. Intraventricular histamine induces the appearances of an arousal EEG pattern in rabbits and increased spontaneous locomotor activity, grooming and exploratory behavior in both saline and pentobarbital-treated rats.

In contrast, a highly selective inhibitor of histidine decarboxylase, the sole enzyme responsible for histamine synthesis, has been shown to impair waking in rats. These data support the hypothesis that histamine may function in modulating behavioral arousal. The role of the $H_3$ receptor in sleep-waking parameters has been demonstrated (Lin et al., 1990) *Brain Res.* 592: 325-330. Oral administration of RAMHA, a $H_3$ agonist, caused a significant increase in deep slow wave sleep in the cat. Conversely, thioperamide, a $H_3$ antagonist/inverse agonist, enhanced wakefulness in a dose-dependent fashion. Thioperamide has also been shown to increase wakefulness and decrease slow-wave and REM sleep in rats. These findings are consistent with in vivo studies demonstrating that thioperamide caused an increase in synthesis and release of histamine. Together, these data demonstrate that selective $H_3$ antagonists or inverse agonists may be useful in the treatment of arousal states and sleep disorders.

Serotonin, histamine, and acetylcholine have all been demonstrated to be diminished in the Alzheimer's (AD) brain. The histamine $H_3$ receptor has been demonstrated to regulate the release of each of these neurotransmitters. An $H_3$ receptor antagonist or inverse agonist would therefore be expected to increase the release of these neurotransmitters in the brain. Since histamine has been demonstrated to be important in arousal and vigilance, $H_3$ receptor antagonists or inverse agonists might enhance arousal and vigilance via increasing levels of neurotransmitter release and thereby improve cognition. Thus, the use of compounds that bind the use of $H_3$ receptor in AD, attention deficit disorders (ADD), age-related memory dysfunction and other cognitive disorders would be supported.

$H_3$ receptor agonists, antagonists or inverse agonists may be useful in treating several other CNS disorders. It has been suggested that histamine may be involved in cerebral circulation, energy metabolism, and hypothalmic hormone secretion. For example, $H_3$ receptor agonists, antagonists or inverse agonists have been demonstrated to affect food intake and body weight gain in rodents. Recent evidence has indicated the possible use of $H_3$ agonists, antagonists or inverse agonists in the treatment of epilepsy. Work has demonstrated an inverse correlation between the duration of clonic convulsions and brain histamine levels. Thioperamide was also shown to significantly and dose-dependently decrease the durations of every convulsive phase after electrically-induced convulsions and increase the electroconvulsive threshold. For examples of therapeutical uses of $H_3$ receptor agonists, inverse agonists or antagonists, see U.S. Pat. No. 6,316,475 or WO 03050099A1.

In spite of their low density, $H_3$ receptor binding sites can be detected outside the brain. Several studies have revealed the presence of $H_3$ heteroreceptors in the gastrointestinal tract, as well as upon neurons of the respiratory tract. Accordingly, an $H_3$ receptor binding compound may be useful in the treatment of diseases and conditions such as asthma, rhinitis, airway congestion, inflammation, hyper and hypo motility and acid secretion of the gastrointestinal tract. Peripheral or central blockage of $H_3$ receptors may also contribute to changes in blood pressure, heart rate and cardiovascular output and could be used in the treatment of cardiovascular diseases, and in the treatment of diseases or conditions such as obesity, migraine, inflammation, motion sickness, pain, ADHD, dementia, depression, Parkinson's disease, schizophrenia, epilepsy, narcolepsy, acute myocardial infarction and asthma.

Various pyrazole derivatives are disclosed in WO 03/024935; WO 03/095430; WO 89/03385; WO 93/23036; EP 0178035; and EP 0647629. For example, both WO 03/024935 and WO 03/095430 disclose certain substituted pyrazolyl compounds for treatment of inflammation. WO 00/19994 and WO 98/27061 disclose various cyclic compounds which may have a spectrum of agonist/antagonist properties.

SUMMARY OF THE INVENTION

The present invention provides, in its principal aspect, compounds of the general formulae:

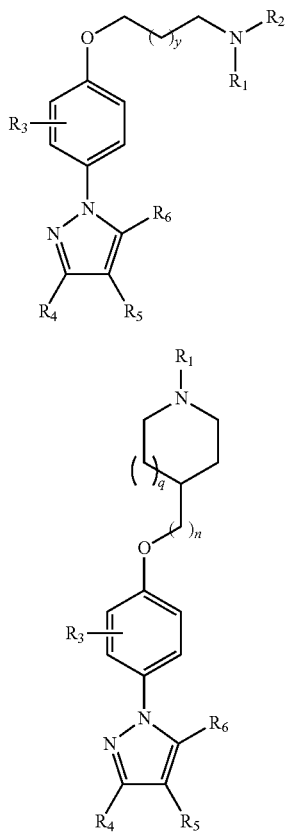

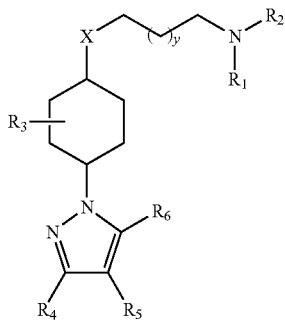

where
X is O or $NR_7$;
y is 0, 1 or 2;
n is 0 or 1
q is 0, 1, or 2;
$R_1$ and $R_2$ are independently selected from the group consisting of $(C_1-C_5)$alkyl and $(C_3-C_6)$cycloalkyl;
or
where X is O, $R_1$ and $R_2$ taken together with the nitrogen to which they are attached form a 5-7 member heterocyclic ring system with 0 or 1 additional hetero atoms selected from O, S, and $NR_6$, wherein the resulting ring may optionally be substituted with 1-3 $(C_1-C_5)$alkyl or $(C_3-C_6)$cycloalkyl groups;
$R_3$ is 0-2 of groups selected from halogen, $(C_1-C_8)$alkyl, $(C_1-C_8)$alkoxy, $(C_3-C_7)$cycloalkyl, $(C_3-C_7)$cycloalkyl-$(C_1-C_6)$alkyl, heterocycloalkyl containing 1-3 hetero atoms selected from O, S, and $(C_1-C_5)$alkyl-O—$(C_1-C_5)$alkyl;
$R_4$ and $R_6$ are independently selected from $(C_1-C_8)$alkyl, $(C_1-C_8)$alkoxy, $(C_3-C_7)$cycloalkyl, $(C_3-C_7)$cycloalkyl-$(C_1-C_6)$alkyl, heterocycloalkyl containing 1-3 hetero atoms selected from O, S, and NH, $(C_1-C_5)$alkyl-O—$(C_1-C_5)$alkyl, amide, $(C_1-C_5)$alkyl-aryl, and $CF_3$;
$R_5$ is selected from the group consisting of hydrogen, $(C_1-C_8)$alkyl, aryl, $(C_1-C_5)$alkyl-O—$(C_1-C_5)$alkyl, and $(C_1-C_5)$alkyl-aryl,
or
$R_5$ and $R_4$ and the atoms to which they are attached form a fused 5-6 member saturated carbocyclic ring or a fused 10 member bi-cyclic ring system, such as

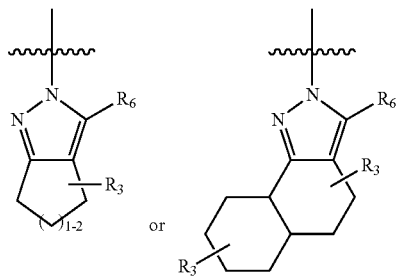

or
$R_5$ and $R_6$ and the atoms to which they are attached form a fused 5-6 member saturated carbocyclic ring or a fused 10 member bi-cyclic ring system, such as

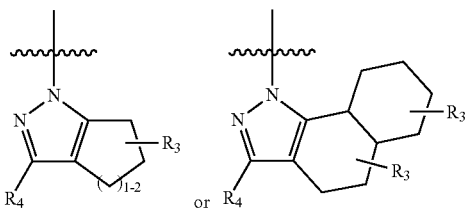

or

R₅ and R₄ and the atoms to which they are attached form a fused 5-6 member saturated carbocyclic ring to which a 6 member aromatic ring is fused, such as

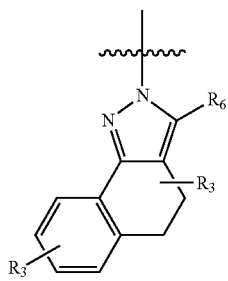

or

R₅ and R₆ and the atoms to which they are attached form a fused 5-6 member saturated carbocyclic ring to which a 6 member aromatic ring is fused, such as

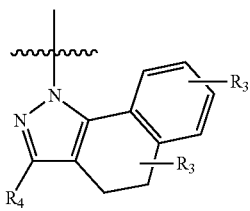

or

R₅ and R₆ and the atoms to which they are attached form a fused benzothiophene or fused benzofuran ring system, such as

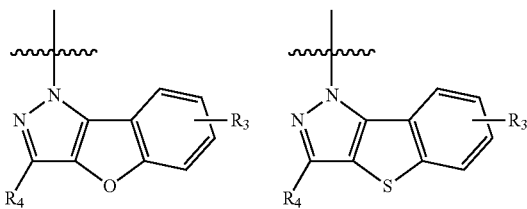

where X is NR₇, R₇ and R₂ taken together are —(CH₂CH₂)— to form a two nitrogen containing ring where y is 0 (piperazine) or y is 1 (homopiperazine), and wherein R₁ is as defined previously, and the pharmaceutically acceptable salts thereof.

This invention also provides pharmaceutical compositions comprising compounds of formulae 1-3, pharmaceutically acceptable salts, solvates, or formulations thereof, and pharmaceutically acceptable carriers in combination with an effective amount of at least one compound of formulae 1-3.

The present invention also provides a method of treating conditions in which modulation of histamine H₃ receptors may be of therapeutic importance such as inflammation, migraine, motion sickness, pain, Parkinson's Disease, epilepsy, cardiovascular disease (i.e. hyper or hypotension, acute myocardial infarction), gastrointestinal disorders (acid secretion, motility) and CNS disorders involving attention or cognitive disorders (i.e., Alzheimer's, Attention Deficit Disorder, age-related memory dysfunction, stroke, etc.), psychiatric disorders (i.e., depression, schizophrenia, obsessive-compulsive disorders, etc.); sleep disorders (i.e. narcolepsy, sleep apnea, insomnia, disturbed biological and circadian rhythms, hyper- and hyposomnolence), and disorders such as obesity, anorexia/bulimia, thermoregulation, hormone release) comprising administering an effective amount of a compound of formulae 1-3 to a patient in need of such treatment.

DETAILED DESCRIPTION OF THE INVENTION

Presently preferred compounds include:
3-Methyl-1-[4-(3-pyrrolidin-1-ylpropoxy)phenyl]-4,5-dihydro-1H-benzo[g]indazole;
3-Methyl-1-{4-[3-(2R-methylpyrrolidin-1-yl)propoxy]phenyl}-4,5-dihydro-1H-benzo[g]indazole;
3-Methyl-1-[4-(3-morpholin-1-ylpropoxy)phenyl]-4,5-dihydro-1H-benzo[g]indazole;
1-[4-(3-Pyrrolidin-1-ylpropoxy)phenyl]-5-styryl-3-trifluoromethyl-1H-pyrazole;
3-Methyl-1-[4-(3-pyrrolidin-1-ylpropoxy)phenyl]-4,5,5a,6,7,8,9,9a-octahydro-1H-benzo[g]indazole;
3-Methyl-2-[4-(3-pyrrolidin-1-ylpropoxy)phenyl]-4,5,5a,6,7,8,9,9a-octahydro-2H-benzo[g]indazole;
8-Methoxy-3-methyl-1-[4-(3-pyrrolidin-1-ylpropoxy)phenyl]-4,5-dihydro-1H-benzo[g]indazole;
7-Methoxy-3-methyl-1-[4-(3-pyrrolidin-1-ylpropoxy)phenyl]-4,5-dihydro-1H-benzo[g]indazole;
6-Methoxy-3-methyl-1-[4-(3-pyrrolidin-1-ylpropoxy)phenyl]-4,5-dihydro-1H-benzo[g]indazole;
2-[4-(1-Cyclopentyl-piperidin-4-yloxy)phenyl]-5-methyl-2H-pyrazole-3-carboxylic acid cyclohexylamide;
2-[4-(1-Cyclohexylpiperidin-4-yloxy)phenyl]-5-methyl-2H-pyrazole-3-carboxylic acid cyclohexylamide;
2-[4-(1-Isopropylpiperidin-4-yloxy)phenyl]-5-methyl-2H-pyrazole-3-carboxylic acid cyclohexylamide;
2-[4-(1-Cyclobutylpiperidin-4-yloxy)phenyl]-5-methyl-2H-pyrazole-3-carboxylic acid cyclohexylamide;
{5-Methyl-2-[4-(3-pyrrolidin-1-ylpropoxy)phenyl]-2H-pyrazol-3-yl}methanol;
5-Cyclopentyloxymethyl-3-methyl-1-[4-(3-pyrrolidin-1-ylpropoxy)phenyl]-1H-pyrazole;
5-Cyclopentyloxymethyl-3-methyl-1-[4-(3-pyrrolidin-1-ylpropoxy)phenyl]-1H-pyrazole;
5-Isopropyloxymethyl-3-methyl-1-[4-(3-pyrrolidin-1-ylpropoxy)phenyl]-1H-pyrazole;
2-[4-(3-Pyrrolidin-1-ylpropoxy)phenyl]-2H-indazole;
4-(4-Methoxyphenyl)-3,5-dimethyl-1-[4-(3-pyrrolidin-1-ylpropoxy)phenyl]-1H-pyrazole;
1-[4-(3-Pyrrolidin-1-ylpropoxy)phenyl]-1H-indazole;
3,5-Diethyl-1-[4-(3-pyrrolidin-1-ylpropoxy)phenyl]-1H-pyrazole;
3,5-Diethyl-1-[4-(3-piperidin-1-ylpropoxy)phenyl]-1H-pyrazole;
3,5-Diethyl-1-[4-(3-morpholin-1-ylpropoxy)phenyl]-1H-pyrazole;
3,5-Diisopropyl-1-[4-(3-pyrrolidin-1-yl-propoxy)-phenyl]-1H-pyrazole;

3,5-Diisopropyl-1-[4-(3-piperidin-1-yl-propoxy)-phenyl]-1H-pyrazole;
3-tert-Butyl-5-methyl-1-[4-(3-pyrrolidin-1-ylpropoxy)-phenyl]-1H-pyrazole;
3-tert-Butyl-5-methyl-1-[4-(3-piperidin-1-ylpropoxy)-phenyl]-1H-pyrazole;
5-Isobutyl-3-methyl-1-[4-(3-pyrrolidin-1-ylpropoxy)-phenyl]-1H-pyrazole;
5-Isobutyl-3-methyl-1-[4-(3-piperidin-1-ylpropoxy)-phenyl]-1H-pyrazole;
5-Isobutyl-3-methyl-1-[4-(3-piperidin-1-ylpropoxy)-phenyl]-2H-pyrazole;
5-Isobutyl-3-methyl-1-[4-(3-pyrrolidin-1-ylpropoxy)-phenyl]-2H-pyrazole;
1-Cyclobutyl-4-[4-(3,5-diisopropylpyrazol-1-yl)phenoxy]piperidine;
5-tert-Butyl-3-methyl-1-[4-(3-pyrrolidin-1-ylpropoxy)-phenyl]-1H-pyrazole;
5-tert-Butyl-3-methyl-1-[4-(3-piperidin-1-ylpropoxy)-phenyl]-1H-pyrazole;
3,5-Dimethyl-1-[4-(3-pyrrolidin-1-ylpropoxy)phenyl]-1H-pyrazole;
3,4,5-Trimethyl-1-[4-(3-pyrrolidin-1-ylpropoxy)phenyl]-1H-pyrazole;
4-Ethyl-3,5-dimethyl-1-[4-(3-pyrrolidin-1-ylpropoxy)phenyl]-1H-pyrazole;
4-Butyl-3,5-dimethyl-1-[4-(3-pyrrolidin-1-ylpropoxy)phenyl]-1H-pyrazole;
4-Phenyl-3,5-dimethyl-1-[4-(3-pyrrolidin-1-ylpropoxy)phenyl]-1H-pyrazole;
5-Methyl-3-phenyl-1-[4-(3-pyrrolidin-1-ylpropoxy)phenyl]-1H-pyrazole;
5-Methyl-3-phenyl-1-[4-(3-pyrrolidin-1-ylpropoxy)phenyl]-2H-pyrazole;
3-tert-Butyl-5-phenyl-1-[4-(3-pyrrolidin-1-ylpropoxy)phenyl]-1H-pyrazole;
3-Phenyl-1-[4-(3-pyrrolidin-1-ylpropoxy)phenyl]-4,5,6,7-tetrahydro-1H-indazole;
3-Phenyl-1-[4-(3-pyrrolidin-1-ylpropoxy)phenyl]-4,5,6,7-tetrahydro-2H-indazole;
5-Furan-2-yl-3-methyl-1-[4-(3-pyrrolidin-1-ylpropoxy)phenyl]-1H-pyrazole;
3-Difluoromethyl-5-furan-2-yl-1-[4-(3-pyrrolidin-1-ylpropoxy)phenyl]-1H-pyrazole;
3-Trifluoromethyl-5-furan-2-yl-1-[4-(3-pyrrolidin-1-ylpropoxy)phenyl]-1H-pyrazole;
3-Trifluoromethyl-5-thiophen-2-yl-1-[4-(3-pyrrolidin-1-ylpropoxy)phenyl]-1H-pyrazole;
3-Difluoromethyl-5-phenyl-1-[4-(3-pyrrolidin-1-ylpropoxy)phenyl]-1H-pyrazole;
5-Phenyl-1-[4-(3-pyrrolidin-1-yl-propoxy)-phenyl]-3-trifluoromethyl-1H-pyrazole;
1-{4-[3-(2-(R)-Methyl-pyrrolidin-1-yl)-propoxy]-phenyl}-5-phenyl-3-trifluoromethyl-1H-pyrazole;
Dimethyl-(1-{3-[4-(5-phenyl-3-trifluoromethyl-pyrazol-1-yl)-phenoxy]-propyl}-pyrrolidin-3-yl)-amine;
4-{3-[4-(5-Phenyl-3-trifluoromethyl-pyrazol-1-yl)-phenoxy]-propyl}-morpholine;
1-{3-[4-(5-Phenyl-3-trifluoromethyl-pyrazol-1-yl)-phenoxy]-propyl}-piperidine;
3-Methyl-1-[4-(3-pyrrolidin-1-yl-propoxy)-phenyl]-4,5,6,7-tetrahydro-1H-indazole;
3-Methyl-2-[4-(3-pyrrolidin-1-yl-propoxy)-phenyl]-4,5,6,7-tetrahydro-2H-indazole;
3-Methyl-1-[4-(3-pyrrolidin-1-yl-propoxy)-phenyl]-1,4,5,6-tetrahydro-cyclopentapyrazole;
3-Methyl-2-[4-(3-pyrrolidin-1-yl-propoxy)-phenyl]-2,4,5,6-tetrahydro-cyclopentapyrazole;
3-Methyl-1-[4-(3-piperidin-1-yl-propoxy)-phenyl]-1,4,5,6-tetrahydro-cyclopentapyrazole;
3-Methyl-2-[4-(3-piperidin-1-yl-propoxy)-phenyl]-2,4,5,6-tetrahydro-cyclopentapyrazole;
3,5-Diisopropyl-1-[2-methyl-4-(3-pyrrolidin-1-ylpropoxy)phenyl]-1H-pyrazole;
3,5-Diisopropyl-1-[2-methyl-4-(3-piperidin-1-ylpropoxy)phenyl]-1H-pyrazole;
5-Benzofuran-2-yl-1-[4-(3-pyrrolidin-1-ylpropoxy)phenyl]-3-trifluoromethyl-1H-pyrazole;
3-Methyl-1-[4-(3-pyrrolidin-1-yl-propoxy)-phenyl]-1H-benzo[4,5]thieno[3,2-c]pyrazole;
3-Methyl-1-{4-[3-(2-methyl-pyrrolidin-1-yl)-propoxy]-phenyl}-1H-benzo[4,5]thieno[3,2-c]pyrazole;
3-[4-(3-Pyrrolidin-1-yl-propoxy)-phenyl]-1-trifluoromethyl-3H-8-oxa-2,3-diazacyclopenta[a]indene;
3-{4-[3-(2-Methyl-pyrrolidin-1-yl)-propoxy]-phenyl}-1-trifluoromethyl-3H-8-oxa-2,3-diazacyclopenta[a]indene;
Dimethyl-(1-{3-[4-(1-trifluoromethyl-8-oxa-2,3-diaza-cyclopenta[a]inden-3-yl)-phenoxy]-propyl}-pyrrolidin-3-yl)-amine;
1-[4-trans-(3,5-Diisopropyl-pyrazol-1-yl)-cyclohexyl]-4-isopropyl-piperazine;
1-[4-cis-(3,5-Diisopropyl-pyrazol-1-yl)-cyclohexyl]-4-isopropyl-piperazine;
3,5-Diisopropyl-1-[trans-4-(3-pyrrolidin-1-yl-propoxy)-cyclohexyl]-1H-pyrazole;
3,5-Diisopropyl-1-[cis-4-(3-pyrrolidin-1-yl-propoxy)-cyclohexyl]-1H-pyrazole;
5-Methyl-2-[4-(3-pyrrolidin-1-yl-propoxy)-phenyl]-2H-pyrazole-3-carboxylic acid cyclohexylamide
5-Methyl-2-{4-[3-(2R-methylpyrrolidin-1-yl)propoxy]phenyl}-2H-pyrazole-3-carboxylic acid cyclohexylamide;
5-Methyl-2-[4-(3-piperidin-1-ylpropoxy)phenyl]-2H-pyrazole-3-carboxylic acid cyclohexylamide;
5-Methyl-2-[4-(3-morpholin-4-ylpropoxy)phenyl]-2H-pyrazole-3-carboxylic acid cyclohexylamide;
5-Methyl-2-{4-[2-(1-methylpyrrolidin-2-yl)ethoxy]phenyl}-2H-pyrazole-3-carboxylic acid cyclohexylamide;
{5-Methyl-2-[4-(3-pyrrolidin-1-ylpropoxy)phenyl]-2H-pyrazol-3-yl}pyrrolidin-1-ylmethanone;
5-Methyl-2-[4-(3-pyrrolidin-1-ylpropoxy)phenyl]-2H-pyrazole-3-carboxylic acid cyclohexylmethylamide;
5-Methyl-2-[4-(3-pyrrolidin-1-ylpropoxy)phenyl]-2H-pyrazole-3-carboxylic acid cyclobutylamide;
5-Methyl-2-[4-(3-pyrrolidin-1-ylpropoxy)phenyl]-2H-pyrazole-3-carboxylic acid phenylamide;
5-Methyl-2-[4-(octahydroquinolizin-1-ylmethoxy)phenyl]-2H-pyrazole-3-carboxylic acid cyclohexylamide; and
5-Methyl-1-[4-(3-pyrrolidin-1-ylpropoxy)phenyl]-1H-pyrazole-3-carboxylic acid cyclohexylamide.

Certain compounds of the invention may exist in different isomeric (e.g. enantiomers and distereoisomers) forms. The invention contemplates all such isomers both in pure form and in a mixture, including racemic mixtures. Enol and tautomeric forms are also included.

The compounds of the invention can exist in unsolvated as well as solvated forms, including hydrated forms, e.g., hemihydrate. In general, the solvated forms, with pharmaceutically acceptable solvents such as water, ethanol, and the like are equivalent to the unsolvated forms for the purposes of the invention.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide, potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.*, 66: 1-19 (1977) which is incorporated herein by reference.

As throughout this specification and appended claims, the following terms have the meanings ascribed to them:

The term "alkyl" as used herein refers to straight or branched chain radicals derived from saturated hydrocarbons by the removal of one hydrogen atom. Representative examples of alkyl groups include methyl, ethyl, n-propyl, iso-propyl, n-butyl, sec-butyl, iso-butyl, tert-butyl, and the like.

The term "cycloalkyl" as used herein refers to an aliphatic ring system having 3 to 10 carbon atoms and 1 to 3 rings, including, but not limited to cyclopropyl, cyclopentyl, cyclohexyl, norbornyl, and adamantly among others. Cycloalkyl groups can be unsubstituted or substituted with one, two or three substituents independently selected from lower alkyl, haloalkyl, alkoxy, thioalkoxy, amino, alkylamino, dialkylamino, hydroxyl, halo, mercapto, nitro, carboxaldehyde, carboxy, alkoxycarbonyl and carboximide.

"Cycloalkyl" includes cis or trans forms. Furthermore, the substituents may either be in endo or exo positions in the bridged bicyclic systems.

The term "halo" or "halogen" as used herein refers to I, Br, Cl or F.

The term "heteroatom" as used herein refers to at least one N, O or S atom.

The term "heterocycloalkyl" as used herein, alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, triflouromethyl, trifluoromethoxy, alkyl, aralkyl, alkenyl, alkynyl, aryl, cyano, carboxy, carboalkoxy, carboxyalkyl, oxo, arylsulfonyl and aralkylaminocarbonyl among others.

As used herein, the term "composition" is intended to encompass a product comprising the specified ingredients in the specified amounts, as well as any product which results, directly or indirectly, from a combination of the specified ingredients in the specified amounts.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. *Pharmaceutical Sciences,* 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate(isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

These compounds have been tested in vitro and in vivo and have been shown to be potent and selective inhibitors of $H_3$ receptor activation. The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; (f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

Compounds of the present invention that are formed by in vivo conversion of a different compound that was administered to a mammal are intended to be included within the scope of the present invention.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The invention may be illustrated by the following representative schemes and examples.

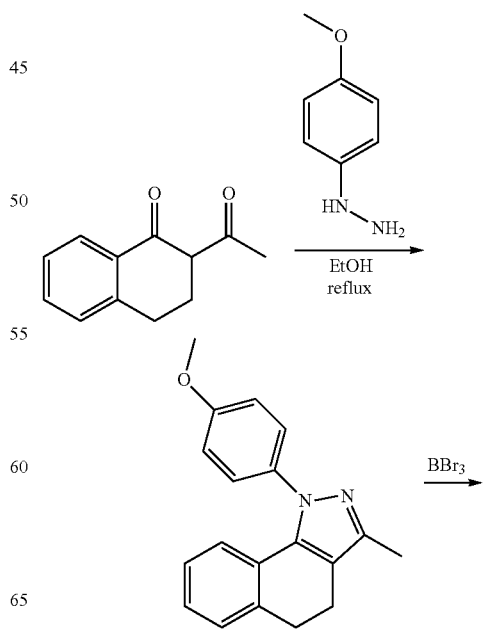

-continued

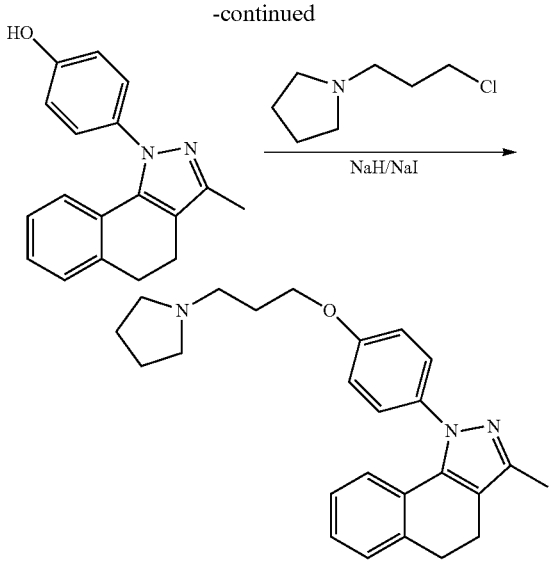

EXAMPLE 1

3-Methyl-1-[4-(3-pyrrolidin-1-ylpropoxy)phenyl]-4,5-dihydro-1H-benzo[g]indazole

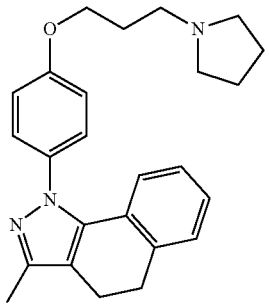

1-(4-Methoxy-phenyl)-3-methyl-4,5-dihydro-1H-benzo[g]indazole. To a solution of 2-acetyl-1-tetralone (329 mg, 1.75 mmol) in ethanol (12 mL) was added 4-methoxyphenyl hydrazine hydrochloride. The stirred suspension was heated to 80° C. overnight. The reaction was cooled to room temperature and diluted with water (100 mL) and extracted with EtOAc (2×50 mL). The combined organic layers were washed with water, 10% NaOH, 10% HCl, brine and dried over $Na_2SO_4$. The solvent was removed under reduced pressure and the residue purified on silica gel using a 5% EtOAc to 25% EtOAc in hexane gradient (yield 396 mg). LC-MS ($C_{19}H_{18}N_2O$ calculated 290) m/z 291 (M+H).

4-(3-Methyl-4,5-dihydrobenzo[g]indazol-1-yl)phenol. 1-(4-Methoxyphenyl)-3-methyl-4,5-dihydro-1H-benzo[g]indazole (200 mg, 0.69 mmol) was dissolved in dichloromethane (2 mL) under $N_2$ and cooled to −40° C. Boron tribromide (2.07 mL, 1 M in dichloromethane, 2.07 mmol) was added dropwise and the solution was stirred for 4 hours, warming to room temperature. The reaction mixture was carefully diluted with saturated $NaHCO_3$ solution. The mixture was extracted with dichloromethane, and the extracts were dried over $MgSO_4$ and concentrated. $SiO_2$ chromatography with 20-80% ethyl acetate/hexanes gave 144 mg of the desired product (76% yield). LC-MS ($C_{18}H_{16}N_2O$ calculated 276) m/z 277 (M+H).

3-Methyl-1-[4-(3-pyrrolidin-1-ylpropoxy)phenyl]-4,5-dihydro-1H-benzo[g]indazole. 4-(3-Methyl-4,5-dihydrobenzo[g]indazol-1-yl)phenol (48 mg, 0.174 mmol) was dissolved in N,N-dimethylformamide (1 mL), and 1-(3-chloropropyl)pyrrolidine (31 mg, 0.21 mmol), sodium hydride (8 mg, 60% dispersion in mineral oil, 0.21 mmol) and sodium iodide (32 mg, 0.21 mmol) were added. The reaction was heated at 70° C. for 1.5 hours, then cooled to room temperature. Saturated sodium bicarbonate solution was added, and the mixture was extracted with ethyl acetate. The extracts were dried over $MgSO_4$ and concentrated. $SiO_2$ chromatography with ethyl acetate, then 2% triethylamine/10% methanol/ethyl acetate gave 27.4 mg of the desired product (40% yield). LC-MS ($C_{25}H_{29}N_3O$ calculated 387) m/z 388 (M+H); $^1$H NMR (300 MHz, $CDCl_3$) δ 7.39-7.34 (m, 2H), 7.27 (d, J=7.5 Hz, 1H), 7.12 (t, J=7.5 Hz, 1H), 7.01-6.93 (m, 3H), 6.81 (d, J=7.8 Hz, 1H), 4.09 (t, J=6.3 Hz, 2H), 2.98 (t, J=6.9 Hz, 2H), 2.74-2.60 (m, 8H), 2.30 (s, 3H), 2.14-2.04 (m, 2H), 1.86-1.82 (m, 4H).

EXAMPLE 2

3-Methyl-1-{4-[3-(2R-methylpyrrolidin-1-yl)propoxy]phenyl}-4,5-dihydro-1H-benzo[g]indazole

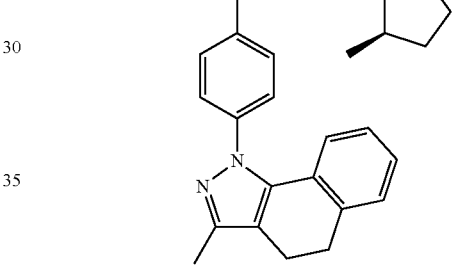

3-Methyl-1-{4-[3-(2R-methylpyrrolidin-1-yl)propoxy]phenyl}-4,5-dihydro-1H-benzo[g]indazole was synthesized by a method analogous to that used for Example 1. LC-MS ($C_{26}H_{31}N_3O$ calculated 401) m/z 402 (M+H).

EXAMPLE 3

3-Methyl-1-[4-(3-morpholin-1-ylpropoxy)phenyl]-4,5-dihydro-1H-benzo[g]indazole

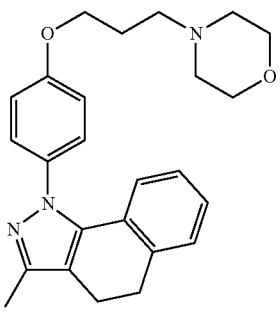

3-Methyl-1-[4-(3-morpholin-1-ylpropoxy)phenyl]-4,5-dihydro-1H-benzo[g]indazole was synthesized by a method analogous to that used for Example 1. LC-MS ($C_{25}H_{29}N_3O_2$ calculated 403) m/z 404 (M+H); $^1$H NMR (300 MHz, CDCl$_3$) δ 7.40 (m, 2H), 7.27 (d, J=6.9 Hz, 1H), 7.12 (dt, J=7.5 Hz, 1.2 Hz, 1H), 7.01-6.93 (m, 3H), 6.81 (d, J=6.9 Hz, 1H), 4.09 (t, J=6.3 Hz, 2H), 3.85-3.77 (m, 4H), 2.98 (t, J=6.9 Hz, 2H), 2.74-2.60 (m, 8H), 2.30 (s, 3H), 2.13-2.04 (m, 2H).

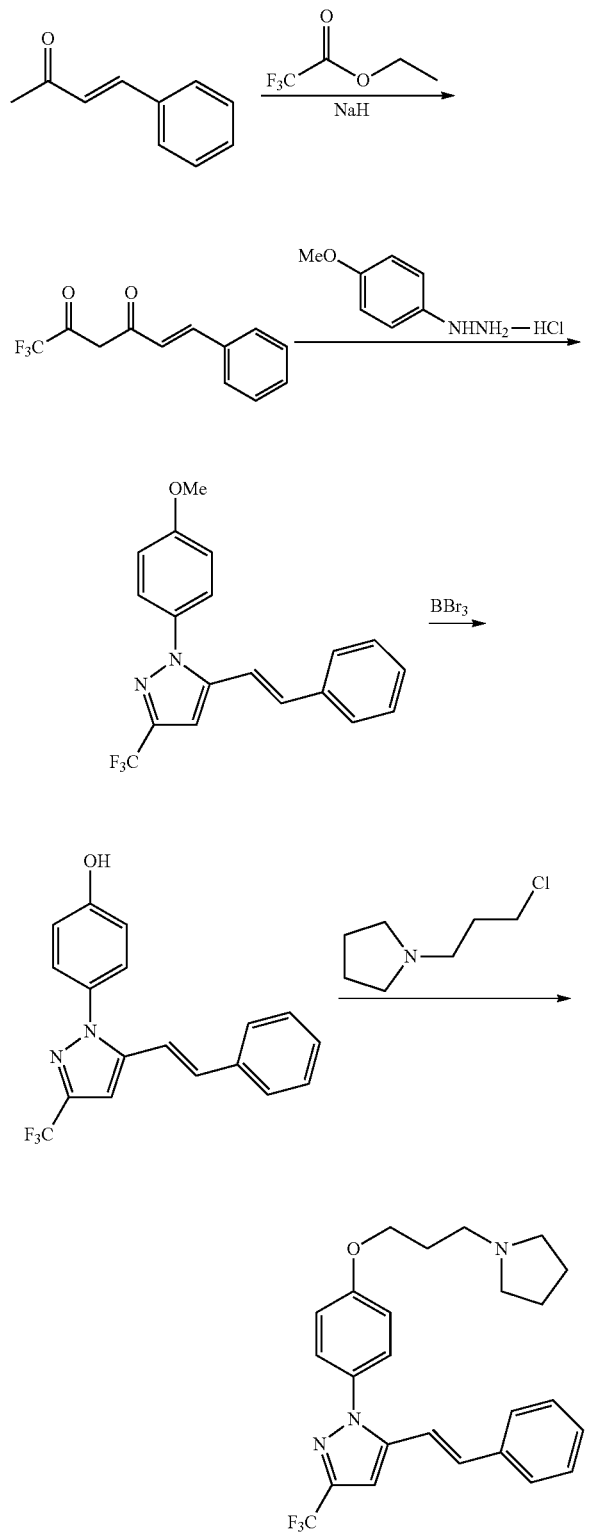

EXAMPLE 4

1-[4-(3-Pyrrolidin-1-ylpropoxy)phenyl]-5-styryl-3-trifluoromethyl-1H-pyrazole

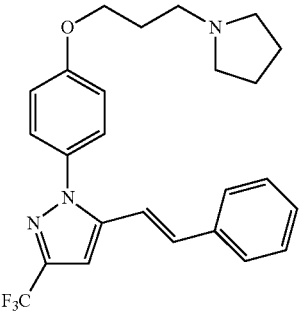

1,1,1-Trifluoro-6-phenylhex-5-ene-2,4-dione. Sodium hydride (547 mg, 60% dispersion in mineral oil, 13.68 mmol) was added to ethyl trifluoroacetate (1.63 mL, 13.68 mmol). (Note: Carefulness is required. The reaction caught fire upon adding sodium hydride to ethyl trifluoroacetate.) Trans-4-Phenyl-3-buten-2-one (1 g, 6.84 mmol) was added, and the reaction was stirred for 3 hours at 40° C. The reaction was cooled to room temperature and quenched with water, then diluted with 1 N HCl. The mixture was extracted with ethyl acetate, dried over MgSO$_4$, and concentrated. The reaction was assumed to be quantitative. LC-MS (C$_{12}$H$_9$F$_3$O$_2$ calculated 242) m/z 243 (M+H).

1-(4-Methoxyphenyl)-5-styryl-3-trifluoromethyl-1H-pyrazole. 1,1,1-Trifluoro-6-phenylhex-5-ene-2,4-dione (2.28 mmol) and 4-methoxyphenylhydrazine hydrochloride (435 mg, 2.5 mmol) were heated in ethanol (7 mL) at 70° C. overnight. The solution was diluted with water and extracted with ethyl acetate. The ethyl acetate extracts were washed with 1 N HCl, saturated sodium bicarbonate solution, and brine, then dried over MgSO$_4$ and concentrated. SiO$_2$ chromatography with 5-20% ethyl acetate/hexanes gave 0.14 g of the desired product, along with many mixed fractions. Only the clean fractions were carried on. LC-MS (C$_{19}$H$_{15}$F$_3$N$_2$O calculated 344) m/z 345 (M+H); $^1$H NMR (300 MHz, CDCl$_3$) δ 7.43-7.30 (m, 7H), 7.12 (d, J=16.2 Hz, 1H), 7.05-7.00 (m, 2H), 6.88 (s, 1H), 6.78 (d, J=16.2 Hz, 1H), 3.89 (s, 3H).

4-(5-Styryl-3-trifluoromethylpyrazol-1-yl)phenol. 1-(4-Methoxyphenyl)-5-styryl-3-trifluoromethyl-1H-pyrazole (0.14 g, 0.4 mmol) was dissolved in dichloromethane (1.2 mL) and cooled to −40° C. Boron tribromide (1.2 mL, 1 M in dichloromethane, 1.2 mmol) was added, and the reaction was stirred overnight, warming up to room temperature. Saturated sodium bicarbonate solution was added, and the mixture was extracted with ethyl acetate. The extracts were dried over MgSO$_4$ and concentrated. The reaction was assumed to be quantitative. LC-MS (C$_{18}$H$_{13}$F$_3$N$_2$O calculated 330) m/z 331 (M+H).

1-[4-(3-Pyrrolidin-1-ylpropoxy)phenyl]-5-styryl-3-trifluoromethyl-1H-pyrazole. 4-(5-Styryl-3-trifluoromethylpyrazol-1-yl)phenol (0.2 mmol) was dissolved in N,N-dimethylformamide (1 mL), and 1-(3-chloropropyl)pyrrolidine (32 mg, 0.22 mmol), sodium hydride (9 mg, 60% dispersion in mineral oil, 0.22 mmol) and sodium iodide (33 mg, 0.22 mmol) were added. The reaction was heated at 70° C. overnight, then cooled to room temperature. Saturated sodium bicarbonate solution was added, and the mixture was extracted with ethyl acetate. The extracts were dried over MgSO$_4$ and concentrated. Semi-prep LC-MS purification gave 20.8 mg of the desired product. LC-MS (C$_{25}$H$_{26}$F$_3$N$_3$O calculated 441) m/z 442 (M+H); $^1$H NMR (300 MHz, CDCl$_3$) δ 7.42-7.30 (m, 7H), 7.12 (d, J=16.2 Hz, 1H), 7.00 (d, J=8.7 Hz, 2H), 6.88 (s, 1H), 6.77 (d, J=16.5 Hz, 1H), 4.10 (t, J=6 Hz, 2H), 2.93-2.86 (m, 6H), 2.21-2.12 (m, 2H), 1.94-1.90 (m, 4H).

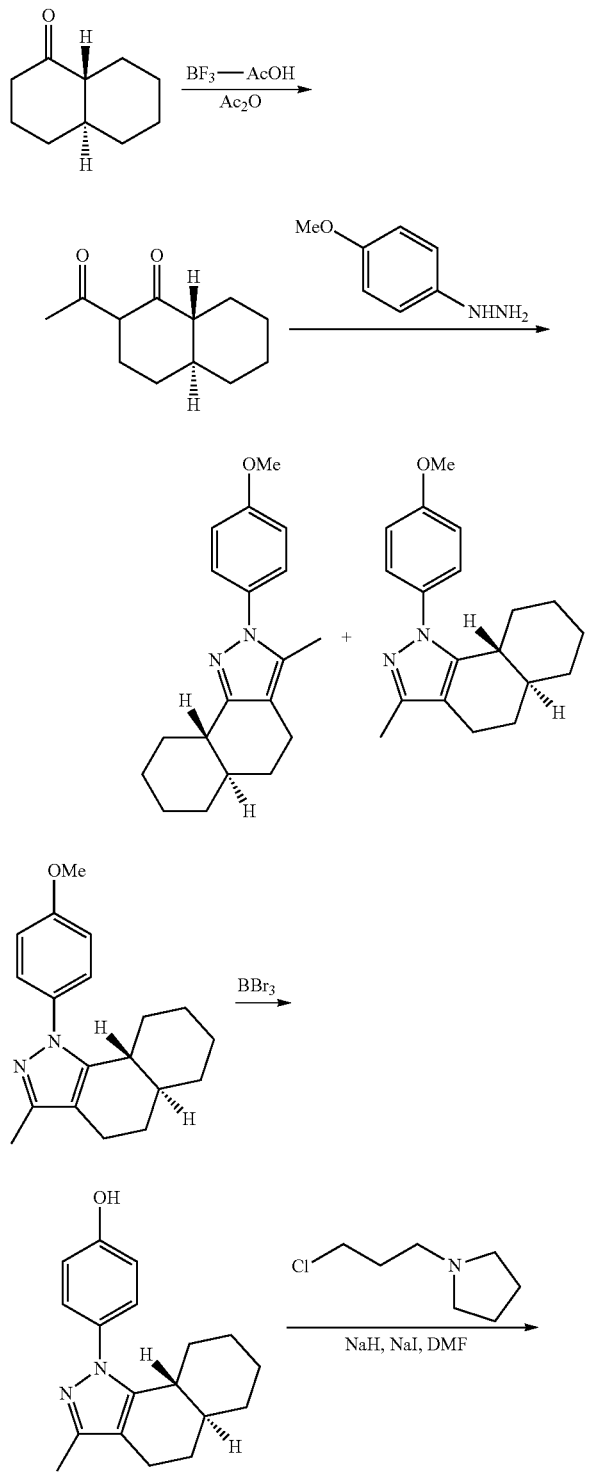

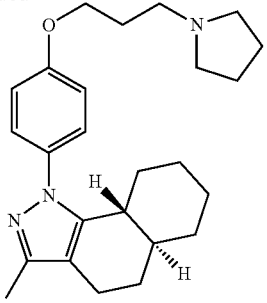

EXAMPLE 5

3-Methyl-1-[4-(3-pyrrolidin-1-ylpropoxy)phenyl]-4,5,5a,6,7,8,9,9a-octahydro-1H-benzo[g]indazole

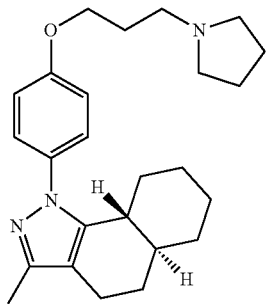

2-Acetyloctahydronaphthalen-1-one. Boron trifluoride-acetic acid complex (5.2 mL, 37.5 mmol) was cooled to 0° C. trans-1-Decalone (3.82 g, 25 mmol) in acetic anhydride (4.7 mL, 50 mmol) was added, and the reaction was stirred at room temperature for 3.5 hours. Saturated ammonium chloride solution (95 mL) was added, and the mixture was heated to 80° C. for 45 minutes. After cooling to room temperature, the mixture was extracted with ethyl acetate. The extracts were dried over MgSO$_4$ and concentrated. SiO$_2$ chromatography with 10-40% ethyl acetate/hexanes gave 0.96 g of the desired product.

2-(4-Methoxyphenyl)-3-methyl-4,5,5a,6,7,8,9,9a-octahydro-2H-benzo[g]indazole and 1-(4-Methoxyphenyl)-3-methyl-4,5,5a,6,7,8,9,9a-octahydro-1H-benzo[g]indazole. 2-Acetyloctahydronaphthalen-1-one (0.96 g, 4.95 mmol) was dissolved in absolute ethanol (10 mL), and 4-methoxyphenylhydrazine hydrochloride (0.95 g, 5.44 mmol) was added. The reaction was stirred overnight at 70° C. The mixture was diluted with water and extracted with ethyl acetate. The organic extracts were washed with 1 N HCl, saturated sodium bicarbonate solution, and brine, then dried over MgSO$_4$ and concentrated. SiO$_2$ chromatography with 5-40% ethyl acetate/hexanes gave 0.15 g of 2-(4-methoxyphenyl)-3-methyl-4,5,5a,6,7,8,9,9a-octahydro-2H-benzo[g]indazole and 0.66 g of 1-(4-methoxyphenyl)-3-methyl-4,5,5a,6,7,8,9,9a-octahydro-1H-benzo[g]indazole. Regiochemistry was determined by x-ray crystal structure of 1-(4-methoxyphenyl)-3-methyl-4,5,5a,6,7,8,9,9a-octahydro-1H-benzo[g]indazole. LC-MS (C$_{19}$H$_{24}$N$_2$O calculated 296) m/z 297 (M+H).

4-(3-Methyl-4,5,5a,6,7,8,9,9a-octahydrobenzo[g]indazol-1-yl)phenol. 1-(4-Methoxyphenyl)-3-methyl-4,5,5a,6,7, 8,9,9a-octahydro-1H-benzo[g]indazole (0.44 g, 1.49 mmol) was dissolved in dichloromethane (4 mL) and cooled to −40° C., and boron tribromide (0.5 mL) was added. The reaction was stirred for 2 hours, then carefully quenched with saturated sodium bicarbonate solution. The mixture was extracted with dichloromethane. The organic extracts were washed with brine, dried over MgSO$_4$, and concentrated. The reaction was assumed to be quantitative. LC-MS (C$_{18}$H$_{22}$N$_2$O calculated 282) m/z 283 (M+H).

3-Methyl-1-[4-(3-pyrrolidin-1-ylpropoxy)phenyl]-4,5,5a,6,7,8,9,9a-octahydro-1H-benzo[g]indazole. 4-(3-Methyl-4,5,5a,6,7,8,9,9a-octahydrobenzo[g]indazol-1-yl)phenol (1.49 mmol) was dissolved in N,N'-dimethylformamide (6 mL), and 1-(3-chloropropyl)pyrrolidine (0.22 g, 1.49 mmol), sodium hydride (72 mg, 60% dispersion in mineral oil, 1.79 mmol) and a catalytic amount of sodium iodide were added. The reaction was heated at 70° C. for 3 hours. The solution was diluted with saturated sodium bicarbonate and extracted with ethyl acetate. The extracts were dried over MgSO$_4$ and concentrated. SiO$_2$ chromatography with 2% triethylamine/10% methanol/ethyl acetate gave 0.268 g of the desired product. LC-MS (C$_{25}$H$_{35}$N$_3$O calc'd 393) m/z 394 (M+H). $^1$H NMR (300 MHz, CDCl$_3$) δ 7.27 (d, J=8.7 Hz, 2H), 6.91 (d, J=9 Hz, 2H), 4.05 (t, J=6.3 Hz, 2H), 2.64 (t, J=7.2 Hz, 2H), 2.58-2.39 (m, 7H), 2.20 (s, 3H), 2.07-2.00 (m, 2H), 1.82-1.10 (m, 14H), 0.91-0.79 (m, 1H).

EXAMPLE 6

3-Methyl-2-[4-(3-pyrrolidin-1-ylpropoxy)phenyl]-4,5,5a,6,7,8,9,9a-octahydro-2H-benzo[g]indazole

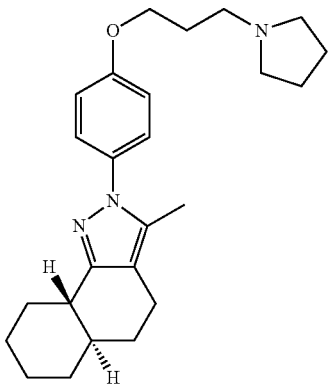

3-Methyl-2-[4-(3-pyrrolidin-1-ylpropoxy)phenyl]-4,5,5a,6,7,8,9,9a-octahydro-2H-benzo[g]indazole was synthesized by a method analogous to that used for Example 5. LC-MS (C$_{25}$H$_{35}$N$_3$O calculated 393) m/z 394 (M+H).

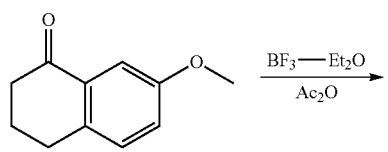

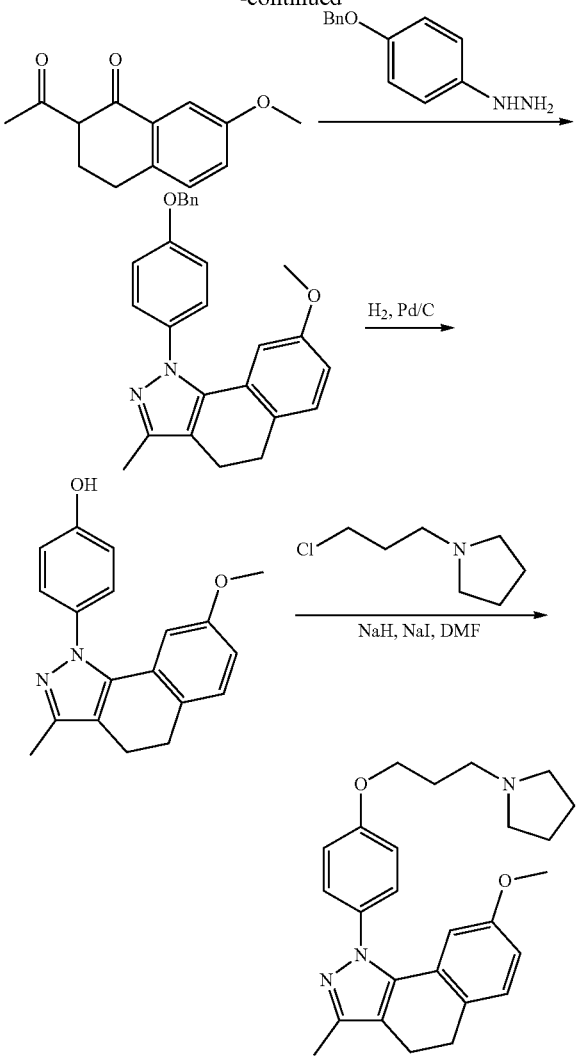

EXAMPLE 7

8-Methoxy-3-methyl-1-[4-(3-pyrrolidin-1-ylpropoxy)phenyl]-4,5-dihydro-1H-benzo[g]indazole

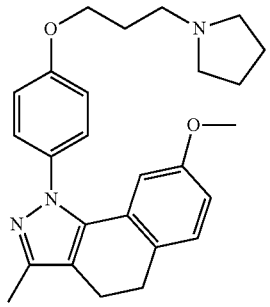

2-Acetyl-7-methoxy-3,4-dihydro-2H-naphthalen-1-one. Boron trifluoride etherate (0.53 mL) was added dropwise to a stirred mixture of 7-methoxytetralone (176 mg, 1 mmol) in acetic anhydride (1.8 mL). The reaction was stirred at room temperature for 2 hours, then poured into ice-water and stirred for 1 hour. The mixture was extracted with ether, and the ether extracts were evaporated. The residue was diluted with methanol (12 mL) and saturated sodium acetate (8 mL) and stirred at reflux for 4 hours. After cooling to room temperature, the solution was extracted with dichloromethane. The organic extracts were washed with brine, dried over $MgSO_4$, and concentrated. $SiO_2$ chromatography with 5-20% ethyl acetate/hexanes gave 72.5 mg of the desired product. LC-MS ($C_{13}H_{14}O_3$ calculated 218) m/z 217 (M–H).

1-(4-Benzyloxyphenyl)-8-methoxy-3-methyl-4,5-dihydro-1H-benzo[g]indazole. 2-Acetyl-7-methoxy-3,4-dihydro-2H-naphthalen-1-one (72.5 mg, 0.33 mmol) and 4-benzyloxyphenylhydrazine hydrochloride (90 mg, 0.36 mmol) were heated in ethanol at 70° C. for 2.5 days. The reaction was diluted with water and extracted with ethyl acetate. The organic extracts were washed with 1 N HCl, saturated sodium bicarbonate solution, and brine, dried over $MgSO_4$, and concentrated. $SiO_2$ chromatography with 5-20% ethyl acetate/hexanes gave 42 mg of the desired product. LC-MS ($C_{26}H_{24}N_2O_2$ calculated 396) m/z 397 (M+H).

4-(8-Methoxy-3-methyl-4,5-dihydrobenzo[g]indazol-1-yl)-phenol. 1-(4-Benzyloxyphenyl)-8-methoxy-3-methyl-4,5-dihydro-1H-benzo[g]indazole (42 mg, 0.1 mmol) was dissolved in methanol/tetrahydrofuran (2/1, v/v, 1.5 mL) and a catalytic amount of 10% Pd/C (wet) was added. The flask was purged with nitrogen and hydrogen, then stirred under 1 atmosphere of hydrogen for 2 hours. The mixture was filtered through Celite and washed with methanol, and the filtrate was concentrated. The reaction was assumed to be quantitative. LC-MS ($C_{19}H_{18}N_2O_2$ calculated 306) m/z 307 (M+H).

8-Methoxy-3-methyl-1-[4-(3-pyrrolidin-1-ylpropoxy)phenyl]-4,5-dihydro-1H-benzo[g]indazole. 4-(8-Methoxy-3-methyl-4,5-dihydrobenzo[g]indazol-1-yl)-phenol (0.1 mmol) was dissolved in N,N-dimethylformamide (1 mL), and -(3-chloropropyl)pyrrolidine (15 mg, 0.1 mmol), sodium hydride (4 mg, 60% dispersion in mineral oil, 0.1 mmol) and sodium iodide (15 mg, 0.1 mmol) were added. The reaction was heated at 70° C. for 3 hours. The solution was diluted with saturated sodium bicarbonate and extracted with ethyl acetate. The extracts were dried over $MgSO_4$ and concentrated. $SiO_2$ chromatography with 2% triethylamine/10% methanol/ethyl acetate gave 8.6 mg of the desired product. LC-MS ($C_{26}H_{31}N_3O_2$ calculated 417) m/z 418 (M+H). $^1$H NMR (300 MHz, $CDCl_3$) δ 7.41-7.36 (m, 2H), 7.17 (d, J=8.7 Hz, 1H), 6.99-6.94 (m, 2H), 6.67 (dd, J=8.7 Hz, 2.4 Hz, 1H), 6.40 (d, J=2.4 Hz, 1H), 4.07 (t, J=6.3 Hz, 2H), 3.52 (s, 3H), 2.91 (m, 2H), 2.72-2.58 (m, 8H), 2.30 (s, 3H), 2.12-2.04 (m, 2H), 1.86-1.81 (m, 4H).

EXAMPLE 8

7-Methoxy-3-methyl-1-[4-(3-pyrrolidin-1-ylpropoxy)phenyl]-4,5-dihydro-1H-benzo[g]indazole

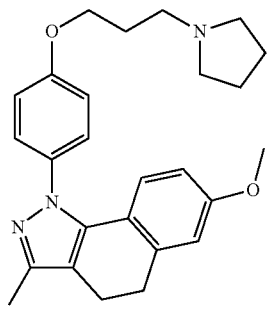

7-Methoxy-3-methyl-1-[4-(3-pyrrolidin-1-ylpropoxy)phenyl]-4,5-dihydro-1H-benzo[g]indazole was synthesized by a method analogous to that used for Example 7. LC-MS ($C_{26}H_{31}N_3O_2$ calc'd 417) m/z 418 (M+H). $^1$H NMR (300 MHz, $CDCl_3$) δ 7.39-7.34 (m, 2H), 6.95-6.90 (m, 2H), 6.83 (d, J=2.7 Hz, 1H), 6.73 (d, J=8.7 Hz, 1H), 6.53 (dd, J=8.7 Hz, 2.7 Hz, 1H), 4.08 (t, J=6 Hz, 2H), 3.77 (s, 3H), 3.12-3.07 (m, 6H), 2.95 (m, 2H), 2.65 (m, 2H), 2.29 (s, 3H), 2.25-2.18 (m, 2H), 2.05-1.96 (m, 4H).

EXAMPLE 9

6-Methoxy-3-methyl-1-[4-(3-pyrrolidin-1-ylpropoxy)phenyl]-4,5-dihydro-1H-benzo[g]indazole

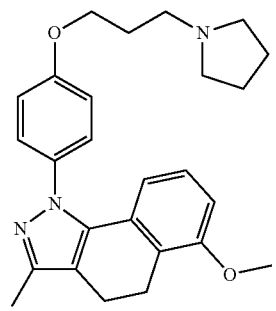

6-Methoxy-3-methyl-1-[4-(3-pyrrolidin-1-ylpropoxy)phenyl]-4,5-dihydro-1H-benzo[g]indazole was synthesized by a method analogous to that used for Example 7. LC-MS ($C_{26}H_{31}N_3O_2$ calc'd 417) m/z 418 (M+H). $^1$H NMR (300 MHz, $CDCl_3$) δ 7.37-7.32 (m, 2H), 6.98-6.91 (m, 3H), 6.75 (d, J=8.1 Hz, 1H), 6.45 (d, J=7.8 Hz, 1H), 4.08 (t, J=6 Hz, 2H), 3.85 (s, 3H), 3.02-2.80 (m, 8H), 2.65-2.60 (m, 2H), 2.30 (s, 3H), 2.19-2.09 (m, 2H), 1.95-1.88 (m, 4H).

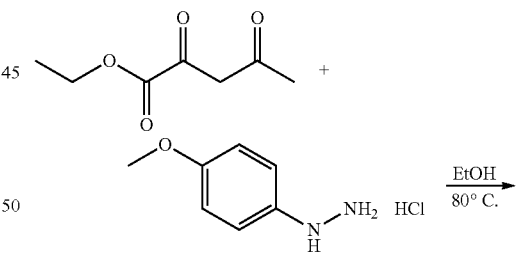

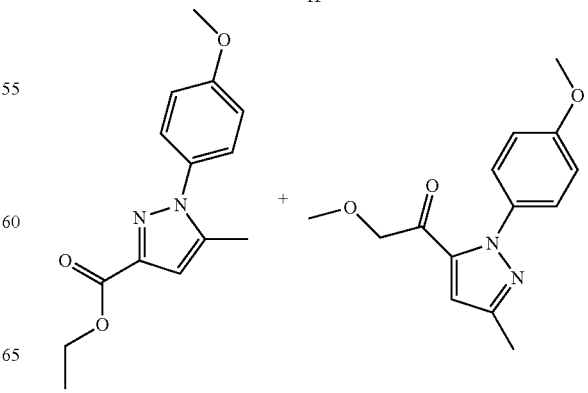

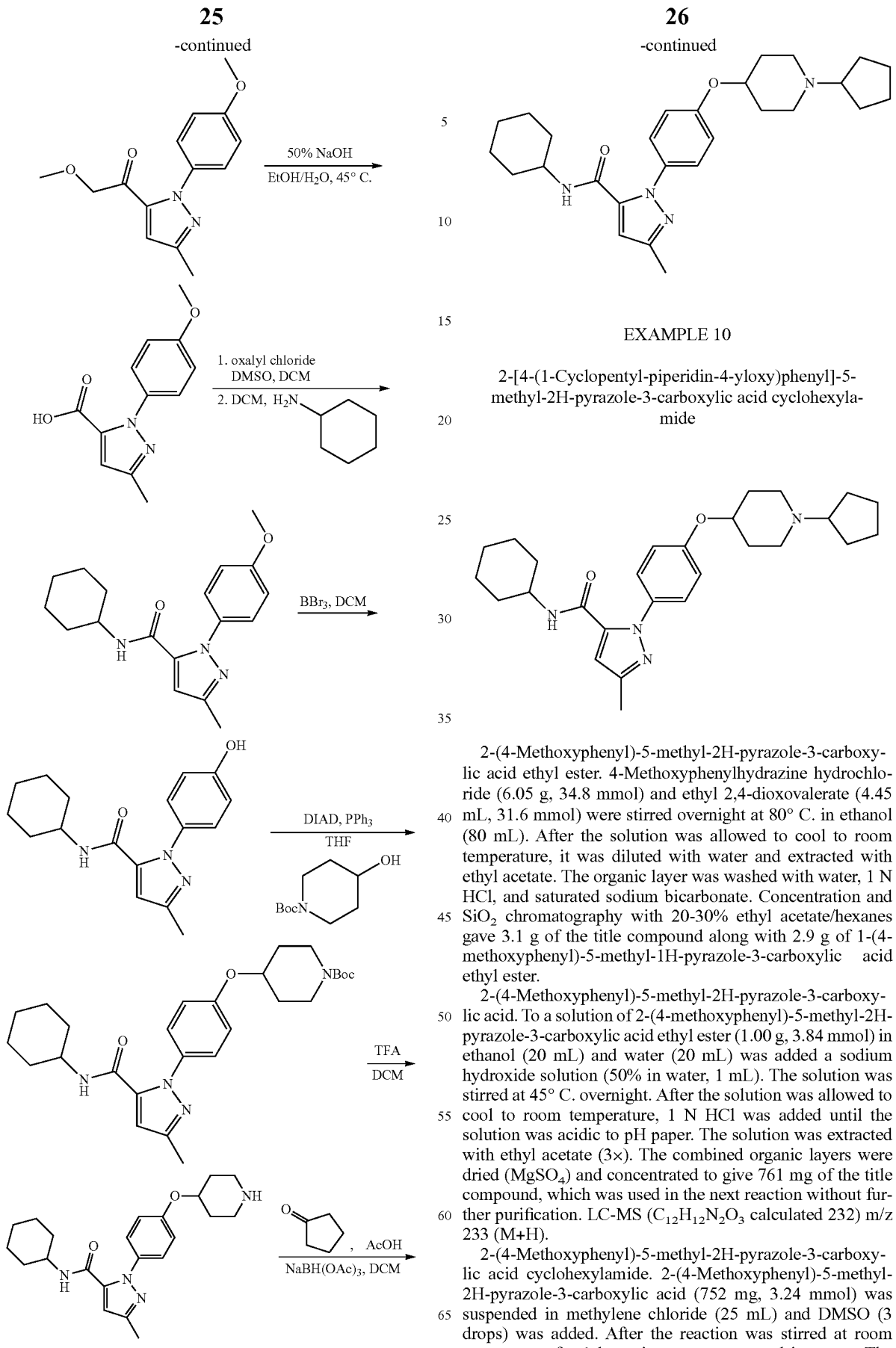

EXAMPLE 10

2-[4-(1-Cyclopentyl-piperidin-4-yloxy)phenyl]-5-methyl-2H-pyrazole-3-carboxylic acid cyclohexylamide 2-(4-Methoxyphenyl)-5-methyl-2H-pyrazole-3-carboxylic acid ethyl ester. 4-Methoxyphenylhydrazine hydrochloride (6.05 g, 34.8 mmol) and ethyl 2,4-dioxovalerate (4.45 mL, 31.6 mmol) were stirred overnight at 80° C. in ethanol (80 mL). After the solution was allowed to cool to room temperature, it was diluted with water and extracted with ethyl acetate. The organic layer was washed with water, 1 N HCl, and saturated sodium bicarbonate. Concentration and SiO$_2$ chromatography with 20-30% ethyl acetate/hexanes gave 3.1 g of the title compound along with 2.9 g of 1-(4-methoxyphenyl)-5-methyl-1H-pyrazole-3-carboxylic acid ethyl ester.

2-(4-Methoxyphenyl)-5-methyl-2H-pyrazole-3-carboxylic acid. To a solution of 2-(4-methoxyphenyl)-5-methyl-2H-pyrazole-3-carboxylic acid ethyl ester (1.00 g, 3.84 mmol) in ethanol (20 mL) and water (20 mL) was added a sodium hydroxide solution (50% in water, 1 mL). The solution was stirred at 45° C. overnight. After the solution was allowed to cool to room temperature, 1 N HCl was added until the solution was acidic to pH paper. The solution was extracted with ethyl acetate (3×). The combined organic layers were dried (MgSO$_4$) and concentrated to give 761 mg of the title compound, which was used in the next reaction without further purification. LC-MS (C$_{12}$H$_{12}$N$_2$O$_3$ calculated 232) m/z 233 (M+H).

2-(4-Methoxyphenyl)-5-methyl-2H-pyrazole-3-carboxylic acid cyclohexylamide. 2-(4-Methoxyphenyl)-5-methyl-2H-pyrazole-3-carboxylic acid (752 mg, 3.24 mmol) was suspended in methylene chloride (25 mL) and DMSO (3 drops) was added. After the reaction was stirred at room temperature for 1 hour, it was concentrated in vacuo. The residue was diluted twice with methylene chloride (60 mL) and concentrated to dryness. The residue was diluted again with methylene chloride (45 mL), cyclohexylamine (650 μL, 5.68 mmol) was added, and the reaction was stirred at room temperature for 1 hour. The reaction was diluted further with methylene chloride, washed with NaOH (10%) and 1 N HCl, then dried over $Na_2SO_4$. Concentration gave 630 mg of the title compound, which was used in the next reaction without further purification. LC-MS ($C_{18}H_{23}N_3O_2$ calculated 313) m/z 314 (M+H).

2-(4-Hydroxyphenyl)-5-methyl-2H-pyrazole-3-carboxylic acid cyclohexylamide. To a solution of 2-(4-methoxyphenyl)-5-methyl-2H-pyrazole-3-carboxylic acid cyclohexylamide (630 mg, 2.01 mmol) in methylene chloride (30 mL) at −40° C. was added boron tribromide (6 mL, 1 M in DCM, 6 mmol). After the reaction was stirred at −40° C. for 10 minutes and at room temperature for 2 hours, it was quenched with saturated sodium bicarbonate. Ethyl acetate was added, and the mixture was stirred for 1 hour. The layers were separated, and the aqueous layer was extracted an additional time with ethyl acetate. The combined organic layers were washed with water and brine, dried ($MgSO_4$), and concentrated to give 600 mg of the title compound which was used in the next reaction without further purification. LC-MS ($C_{17}H_{21}N_3O_2$ calculated 299) m/z 300 (M+H).

4-[4-(5-Cyclohexylcarbamoyl-3-methylpyrazol-1-yl)phenoxy]piperidine-1-carboxylic acid tert-butyl ester. To a solution of 2-(4-hydroxyphenyl)-5-methyl-2H-pyrazole-3-carboxylic acid cyclohexylamide (300 mg, 1.00 mmol) and triphenylphosphine (291 mg, 1.11 mmol) in tetrahydrofuran (5 mL) was added 1-tert-butoxycarbonyl-4-hydroxypiperidine (221 mg, 1.10 mmol) followed by dropwise addition of diisopropylazodicarboxylate (216 μL, 1.10 mmol). The solution was stirred at room temperature overnight, concentrated and dissolved in ethyl acetate. The ethyl acetate was washed with water, dried ($MgSO_4$) and concentrated to give the crude product in quantitative yield. LC-MS ($C_{27}H_{38}N_4O_4$ calculated 482) m/z 483 (M+H).

5-Methyl-2-[4-(piperidin-4-yloxy)phenyl]-2H-pyrazole-3-carboxylic acid cyclohexylamide. To a solution of 4-[4-(5-cyclohexylcarbamoyl-3-methylpyrazol-1-yl)phenoxy]piperidine-1-carboxylic acid tert-butyl ester (482 mg, 1.00 mmol) in methylene chloride (10 mL) was added trifluoroacetic acid (2 mL). After the reaction was stirred at room temperature for 2 hours, it was quenched with saturated sodium bicarbonate and the aqueous layer was extracted with methylene chloride. The combined organic layers were dried ($MgSO_4$) and concentrated to give the crude product in quantitative yield. LC-MS ($C_{22}H_{30}N_4O_2$ calculated 382) m/z 383 (M+H).

2-[4-(1-Cyclopentylpiperidin-4-yloxy)phenyl]-5-methyl-2H-pyrazole-3-carboxylic acid cyclohexylamide. To a solution of 5-methyl-2-[4-(piperidin-4-yloxy)phenyl]-2H-pyrazole-3-carboxylic acid cyclohexylamide (60 mg, 0.157 mmol) in methylene chloride (9 mL) was added cyclopentanone (21 μL, 0.24 mmol) and acetic acid (150 μL). After 1 hour at room temperature, sodium triacetoxyborohydride (51 mg, 0.24 mmol) was added and the reaction was allowed to stir for an additional 4 hours. The reaction was quenched with 10% NaOH and extracted with methylene chloride. The methylene chloride solution was dried ($MgSO_4$) and concentrated. The residue was purified by semi-prep LC-MS to give 2.4 mg of the desired product. LC-MS ($C_{27}H_{38}N_4O_2$ calculated 450) m/z 451 (M+H); $^1H$ NMR (300 MHz, $CDCl_3$) δ 7.34-7.31 (m, 2H), 7.01-6.98 (m, 2H), 6.78 (d, J=8.4 Hz, 1H), 6.70 (s, 1H), 4.42 (m, 1H), 3.95-3.93 (m, 1H), 2.87-2.83 (m, 2H), 2.68-2.54 (m, 3H), 2.23 (s, 3H), 2.15-1.14 (m, 22H).

EXAMPLE 11

2-[4-(1-Cyclohexylpiperidin-4-yloxy)phenyl]-5-methyl-2H-pyrazole-3-carboxylic acid cyclohexylamide

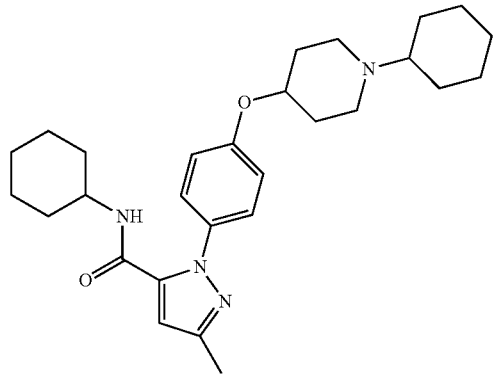

2-[4-(1-Cyclohexylpiperidin-4-yloxy)phenyl]-5-methyl-2H-pyrazole-3-carboxylic acid cyclohexylamide was synthesized by a method analogous to that used for Example 10. LC-MS ($C_{28}H_{40}N_4O_2$ calculated 464) m/z 465 (M+H).

EXAMPLE 12

2-[4-(1-Isopropylpiperidin-4-yloxy)phenyl]-5-methyl-2H-pyrazole-3-carboxylic acid cyclohexylamide

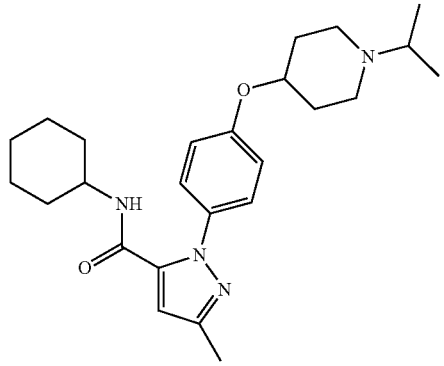

2-[4-(1-Isopropylpiperidin-4-yloxy)phenyl]-5-methyl-2H-pyrazole-3-carboxylic acid cyclohexylamide was synthesized by a method analogous to that used for Example 10. LC-MS ($C_{25}H_{36}N_4O_2$ calculated 424) m/z 425 (M+H).

EXAMPLE 13

2-[4-(1-Cyclobutylpiperidin-4-yloxy)phenyl]-5-methyl-2H-pyrazole-3-carboxylic acid cyclohexylamide

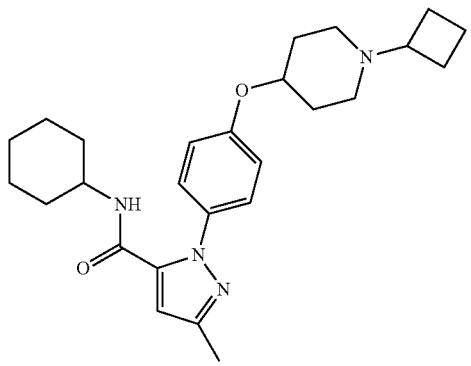

2-[4-(1-Cyclobutylpiperidin-4-yloxy)phenyl]-5-methyl-2H-pyrazole-3-carboxylic acid cyclohexylamide was synthesized by a method analogous to that used for Example 10. LC-MS ($C_{26}H_{36}N_4O_2$ calculated 436) m/z 437 (M+H).

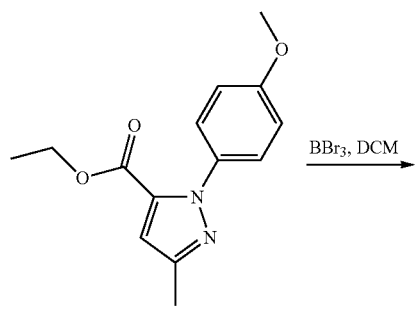

BBr₃, DCM

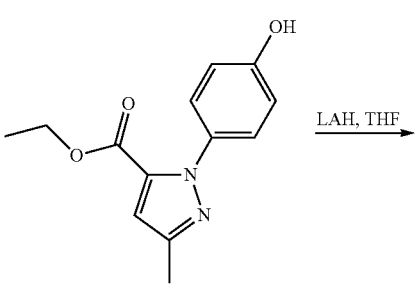

LAH, THF

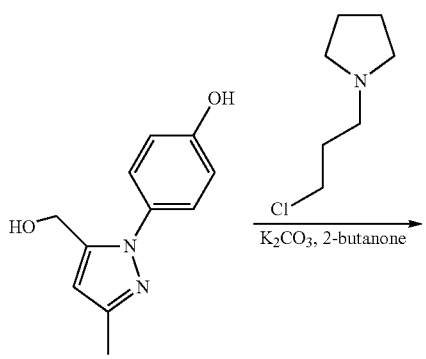

K₂CO₃, 2-butanone

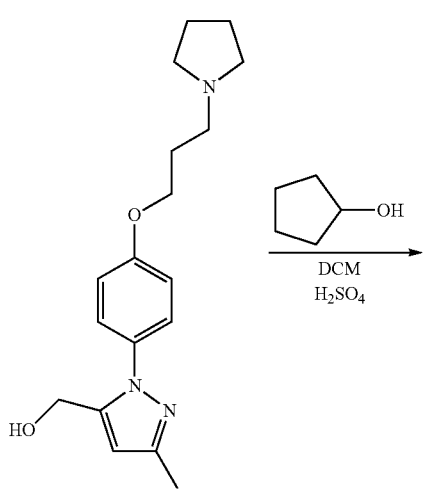

DCM
H₂SO₄

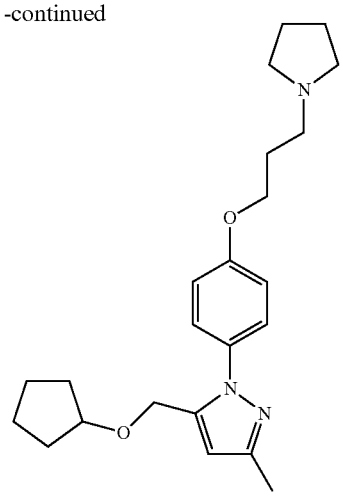

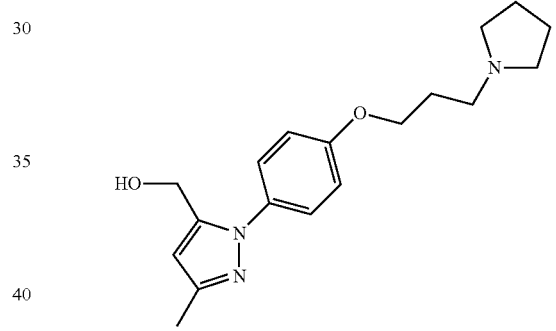

EXAMPLE 14

{5-Methyl-2-[4-(3-pyrrolidin-1-ylpropoxy)phenyl]-2H-pyrazol-3-yl}methanol 2-(4-Hydroxyphenyl)-5-methyl-2H-pyrazole-3-carboxylic acid ethyl ester. To a solution of 2-(4-methoxyphenyl)-5-methyl-2H-pyrazole-3-carboxylic acid ethyl ester (200 mg, 0.768 mmol, Example 10, Step 1) in methylene chloride (10 mL) at −40° C. was added boron tribromide (2.3 mL). The reaction was allowed to stir for 1 hour at −40° C. and for an additional hour while warming to room temperature. The reaction was quenched with ethanol diluted with water and methylene chloride. The organic layer was dried (MgSO₄) and concentrated to give 128 mg of the desired product. LC-MS ($C_{13}H_{14}N_2O_3$ calculated 246) m/z 247 (M+H).

4-(5-Hydroxymethyl-3-methyl-pyrazol-1-yl)-phenol. 2-(4-Hydroxyphenyl)-5-methyl-2H-pyrazole-3-carboxylic acid ethyl ester (233 mg, 0.946 mmol) was dissolved in tetrahydrofuran (20 mL). Lithium aluminum hydride (1.42 mL, 1 M in THF, 1.42 mmol) was added, and the reaction was stirred overnight. The reaction was quenched with water and extracted with ethyl acetate. The ethyl acetate solution was dried (MgSO₄) and concentrated to give the crude product in quantitative yield. LC-MS ($C_{11}H_{12}N_2O_2$ calculated 204) m/z 205 (M+H).

{5-Methyl-2-[4-(3-pyrrolidin-1-ylpropoxy)phenyl]-2H-pyrazol-3-yl}methanol. To a solution of 4-(5-hydroxymethyl-3-methylpyrazol-1-yl)phenol (326 mg, 1.60 mmol) in 2-butanone (8 mL) was added potassium carbonate (243 mg, 1.76 mmol) and 1-(3-chloropropyl)pyrrolidine (260 mg, 1.76 mmol). The reaction was heated overnight at 80° C. After the reaction was diluted with water and extracted with methylene chloride, the organic layer was dried (MgSO$_4$) and concentrated to give 315 mg of the desired product. LC-MS (C$_{18}$H$_{25}$N$_3$O$_2$ calculated 315) m/z 316 (M+H).

EXAMPLE 15

5-Cyclopentyloxymethyl-3-methyl-1-[4-(3-pyrrolidin-1-yl-propoxy)phenyl]-1H-pyrazole

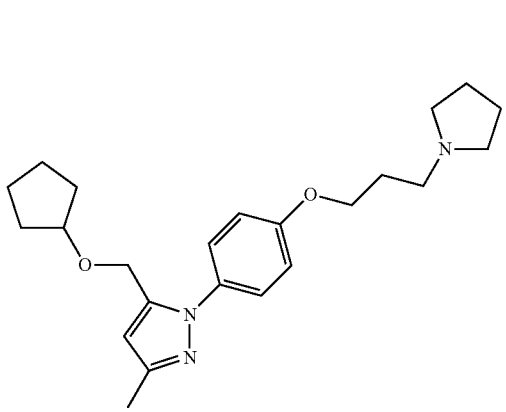

A solution of {5-methyl-2-[4-(3-pyrrolidin-1-ylpropoxy)phenyl]-2H-pyrazol-3-yl}methanol (20 mg, 0.063 mmol, Example 14), cyclopropanol (115 μL, 1.26 mmol) and sulfuric acid (50 μL) in methylene chloride (2 mL) was heated at 40° C. for 7 hours. The reaction was diluted with water and methylene chloride. The organic layer was dried (MgSO$_4$) and concentrated. The residue was purified by semi-prep LC-MS to give 0.5 mg of the desired product. LC-MS (C$_{23}$H$_{33}$N$_3$O$_2$ calc'd 383) m/z 384 (M+H); $^1$H NMR (300 MHz, CDCl$_3$) δ 7.31 (d, J=9.0 Hz, 2H), 6.94 (d, J=9.0 Hz, 2H), 6.21 (s, 1H), 4.48 (s, 2H), 4.06 (t, J=6.3 Hz, 3H), 2.85-2.78 (m, 6H), 2.26 (s, 3H), 2.16-1.26 (m, 14H).

EXAMPLE 16

5-Cyclopentyloxymethyl-3-methyl-1-[4-(3-pyrrolidin-1-ylpropoxy)phenyl]-1H-pyrazole

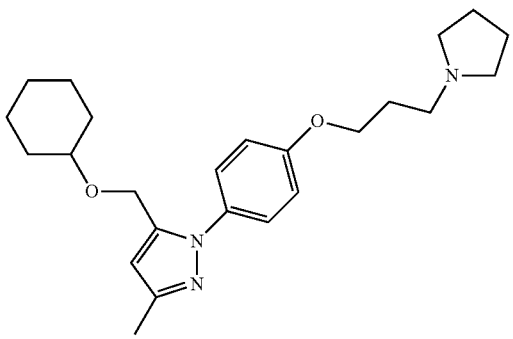

5-Cyclohexyloxymethyl-3-methyl-1-[4-(3-pyrrolidin-1-ylpropoxy)phenyl]-1H-pyrazole was synthesized by a method analogous to that used for example 15. LC-MS (C$_{24}$H$_{35}$N$_3$O$_2$ calculated 397) m/z 398 (M+H).

EXAMPLE 17

5-Isopropyloxymethyl-3-methyl-1-[4-(3-pyrrolidin-1-ylpropoxy)phenyl]-1H-pyrazole

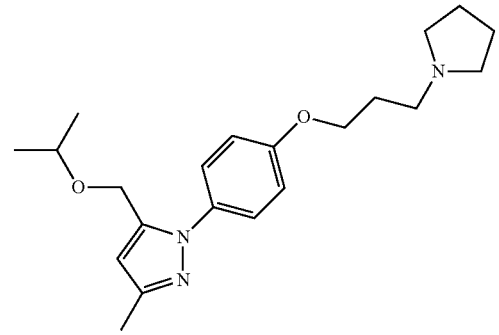

5-Cyclohexyloxymethyl-3-methyl-1-[4-(3-pyrrolidin-1-ylpropoxy)phenyl]-1H-pyrazole was synthesized by a method analogous to that used for Example 15. LC-MS (C$_{21}$H$_{31}$N$_3$O$_2$ calculated 357) m/z 358 (M+H).

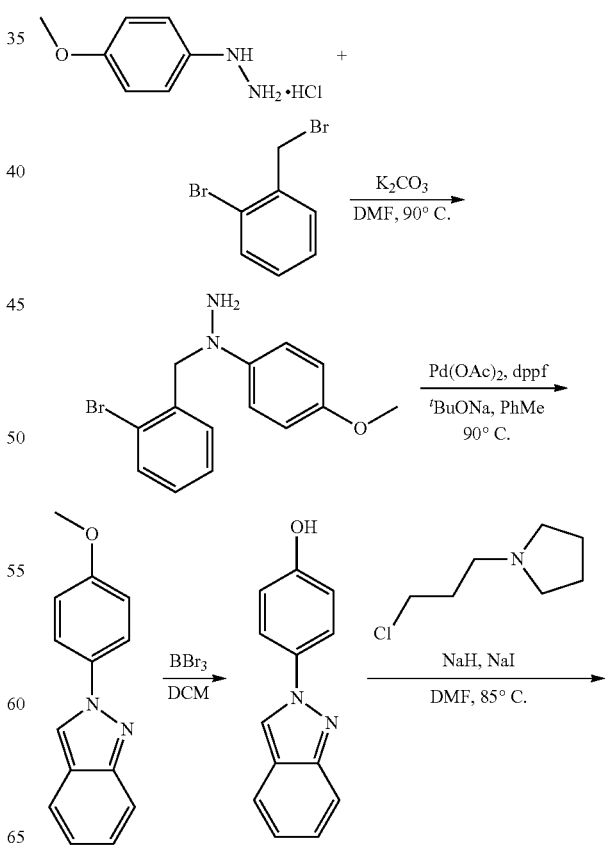

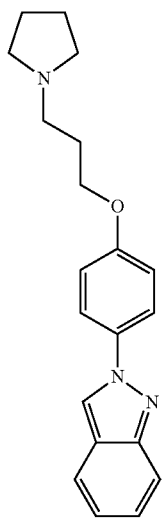

EXAMPLE 18

2-[4-(3-Pyrrolidin-1-ylpropoxy)phenyl]-2H-indazole

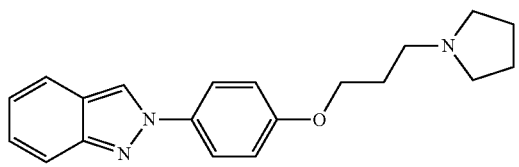

N-(2-Bromobenzyl)-N-(4-methoxyphenyl)hydrazine. To a suspension of 2-bromobenzyl bromide (500 mg, 2.00 mmol) and 4-methoxyphenylhydrazine hydrochloride (348 mg, 2.00 mmol) in N,N-dimethylformamide (8 mL) was added potassium carbonate (1.38 g, 10.0 mmol). The reaction mixture was heated at 90° C. for 4 hours. The reaction was partitioned between water and methylene chloride. The methylene chloride was dried (MgSO$_4$), concentrated and purified by SiO$_2$ chromatography with 10-50% ethyl acetate/hexanes to give 298 mg of the title compound. LC-MS ($C_{14}H_{18}BrN_2O$ calculated 306) m/z 307 (M+H).

2-(4-Methoxyphenyl)-2H-indazole. 2-(4-Methoxyphenyl)-2H-indazole was prepared according to Song and Yee (Org. Lett. 2000, 2, 519). To a solution of N-(2-bromobenzyl)-N-(4-methoxyphenyl)hydrazine (298 mg, 0.97 mmol) in toluene (3.5 mL) were added palladium acetate (11 mg, 0.05 mmol), 1,1'-bis(diphenylphosphino)ferrocene (46 mg, 0.075 mmol) and sodium tert-butoxide (140 mg, 1.46 mmol). The vial was capped and the reaction was stirred at 90° C. overnight. After the reaction was allowed to cool, it was filtered through a pad of silica and concentrated to give the desired product. The reaction was assumed to be quantitative. LC-MS ($C_{14}H_{12}N_2O$ calculated 224) m/z 225 (M+H).

4-Indazol-2-ylphenol. To a solution of 2-(4-methoxyphenyl)-2H-indazole (50 mg, 0.22 mmol) in methylene chloride (3 mL) at −78° C. was added boron tribromide (62 µL, 0.66 mmol). The reaction was stirred at −78° C. for 1 hour and room temperature for 1 hour. The reaction was quenched with saturated sodium bicarbonate solution. After the aqueous layer was extracted with methylene chloride, the combined organic layers were dried (MgSO$_4$) and concentrated to give 28.4 mg of the desired indazole. LC-MS ($C_{13}H_{10}N_2O$ calculated 210) m/z 211 (M+H).

2-[4-(3-Pyrrolidin-1-ylpropoxy)phenyl]-2H-indazole. To a solution of 4-Indazol-2-ylphenol (28 mg, 0.13 mmol) and sodium iodide (6 mg, 0.04 mmol) in N,N-dimethylformamide (3 mL) was added sodium hydride (8.0 mg, 60% in mineral oil, 0.2 mmol) followed by 1-(3-chloropropyl)pyrrolidine (30 mg, 0.20 mmol). After the reaction was heated at 85° C. overnight and allowed to cool, it was partitioned between water and methylene chloride. The organic layer was dried (MgSO$_4$), concentrated and purified by semi-prep LC-MS to give 5.0 mg of the desired indazole. LC-MS ($C_{20}H_{23}N_3O$ calc'd 321) m/z 322 (M+H); $^1$H NMR (300 MHz, CDCl$_3$) δ 8.33 (s, 1H), 7.81-7.77 (m, 3H), 7.71 (d, J=8.7 Hz, 1H), 7.34-7.29 (m, 1H), 7.14-7.09 (m, 1H), 7.05-7.02 (m, 2H), 4.10 (t, J=6.6 Hz, 2H), 2.72 (t, J=7.2 Hz, 2H), 2.63 (m, 4H), 2.08 (quint, J=6.3 Hz, 2H), 1.86-1.81 (m, 4H).

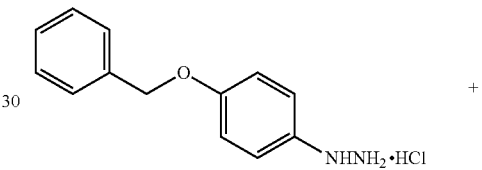

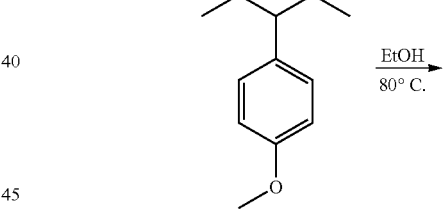

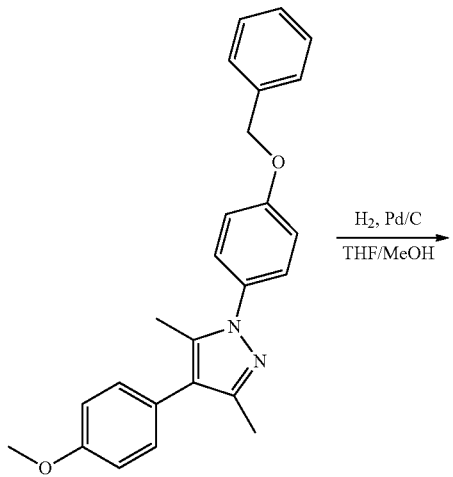

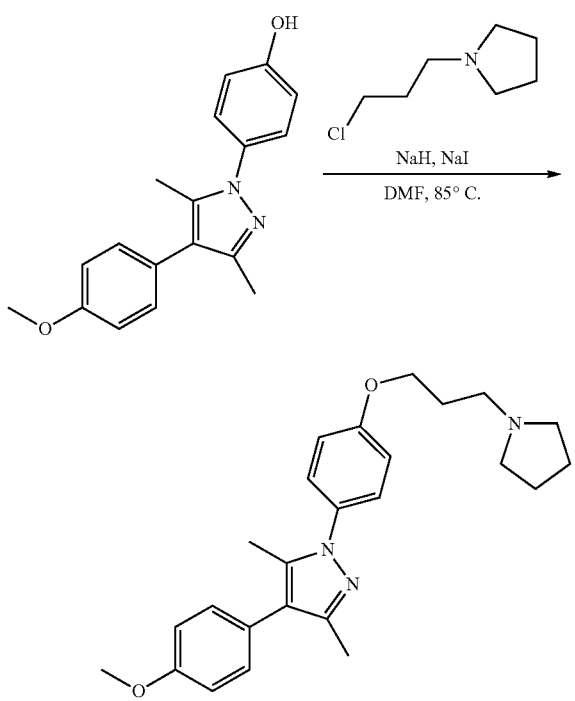

EXAMPLE 19

4-(4-Methoxyphenyl)-3,5-dimethyl-1-[4-(3-pyrrolidin-1-ylpropoxy)phenyl]-1H-pyrazole

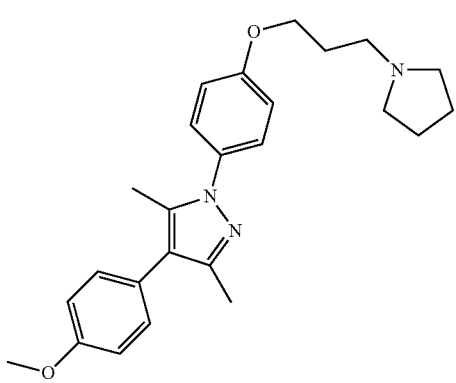

1-(4-Benzyloxyphenyl)-4-(4-methoxyphenyl)-3,5-dimethyl-1H-pyrazole. A solution of 3-(4-methoxyphenyl)pentane-2,4-dione (50 mg, 0.24 mmol, prepared according to Ghosh et al, Bioorg. Med. Chem. 2003, 11, 629) and (4-benzyloxyphenyl)hydrazine hydrochloride (61 mg, 0.24 mmol) in ethanol (3 mL) was heated at 80° C. overnight. The reaction was diluted with water and extracted with ethyl acetate. The organic layer was washed with 1 N HCl (2×) and saturated sodium bicarbonate (1×), dried (MgSO$_4$), and concentrated to give 57 mg of the crude pyrazole. LC-MS (C$_{25}$H$_{24}$N$_2$O$_2$ calculated 384) m/z 385 (M+H).

4-[4-(4-Methoxyphenyl)-3,5-dimethylpyrazol-1-yl]phenol. A solution of 1-(4-benzyloxyphenyl)-4-(4-methoxyphenyl)-3,5-dimethyl-1H-pyrazole (57 mg, 0.15 mmol) in methanol (2 mL) and tetrahydrofuran (3 mL) was flushed with nitrogen. A catalytic amount of palladium on carbon (10% wet) was added, and the reaction was again flushed with nitrogen followed by hydrogen. After the reaction was allowed to stir at room temperature for 1 hour, it was filtered through a pad of Celite and concentrated to give 37 mg of the desired phenol. LC-MS (C$_{18}$H$_{18}$N$_2$O$_2$ calculated 294) m/z 295 (M+H).

4-(4-Methoxyphenyl)-3,5-dimethyl-1-[4-(3-pyrrolidin-1-ylpropoxy)phenyl]-1H-pyrazole. To a solution of 4-[4-(4-methoxyphenyl)-3,5-dimethylpyrazol-1-yl]phenol (37 mg, 0.13 mmol) and sodium iodide (6 mg, 0.04 mmol) in N,N-dimethylformamide (3 mL) was added sodium hydride (8.0 mg, 60% in mineral oil, 0.2 mmol) followed by 1-(3-chloropropyl)pyrrolidine (30 mg, 0.20 mmol). After the reaction was heated at 85° C. overnight and allowed to cool, it was partitioned between water and methylene chloride. The organic layer was dried (MgSO$_4$), concentrated and purified by semi-prep LC-MS to give 2.4 mg of the desired indazole. LC-MS (C$_{25}$H$_{31}$N$_3$O$_2$ calculated 405) m/z 406 (M+H); $^1$H NMR (300 MHz, CDCl$_3$) δ 7.37-7.34 (m, 2H), 7.26-7.22 (m, 2H), 6.99-6.96 (m, 4H), 4.07 (t, J=6.3 Hz, 2H), 3.85 (s, 3H), 2.70 (t, J=7.2 Hz, 2H), 2.61 (m, 4H), 2.31 (s, 3H), 2.23 (s, 3H), 2.06 (quint, J=6.3 Hz, 2H), 1.85-1.80 (m, 4H).

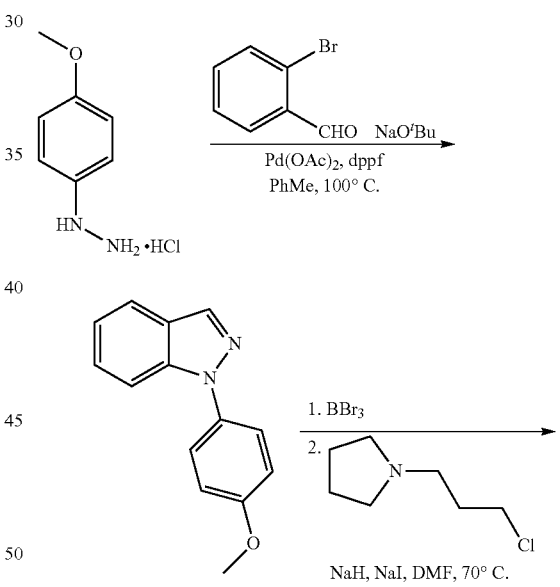

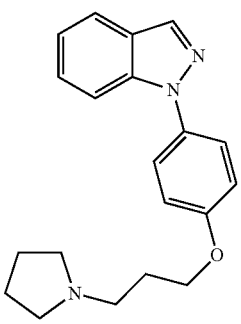

EXAMPLE 20

1-[4-(3-Pyrrolidin-1-ylpropoxy)phenyl]-1H-indazole

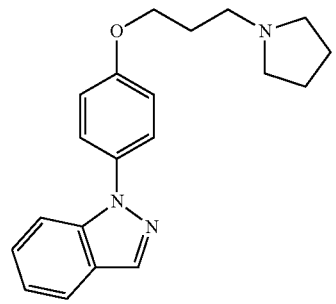

1-(4-Methoxyphenyl)-1H-indazole. 2-Bromobenzaldehyde (74 mg, 0.4 mmol), 4-methoxyphenylhydrazine hydrochloride (70 mg, 0.4 mmol), sodium tert-butoxide (115 mg, 1.2 mmol), palladium(II) acetate (18 mg, 0.08 mmol) and 1,1'-bis(diphenylphosphino)ferrocene (44 mg, 0.08 mmol) were dissolved in toluene (0.6 mL) and heated to 100° C. overnight. The mixture was filtered through Celite with ethyl acetate, and the filtrate was concentrated. SiO$_2$ chromatography (5-20% ethyl acetate/hexanes) gave the desired product, 30 mg. LC-MS (C$_{14}$H$_{12}$N$_2$O calculated 224) m/z 225 (M+H).

4-Indazol-1-yl-phenol. 1-(4-Methoxyphenyl)-1H-indazole (30 mg, 0.134 mmol) was dissolved in dichloromethane (0.4 mL) and cooled to −40° C. Boron tribromide (0.4 mL, 1 M solution in dichloromethane, 0.4 mmol) was added, and the reaction was warmed to rt and stirred for 5 hours. Saturated sodium bicarbonate solution was added, and the mixture was extracted with dichloromethane. The extracts were dried over MgSO$_4$ and concentrated to give the desired product. LC-MS (C$_{13}$H$_{10}$N$_2$O calculated 210) m/z 211 (M+H).

1-[4-(3-Pyrrolidin-1-ylpropoxy)phenyl]-1H-indazole. 4-Indazol-1-yl-phenol (0.07 mmol) was dissolved in N,N'dimethylformamide (0.5 mL), and sodium hydride (3 mg, 60% dispersion in mineral oil, 0.085 mmol), 1-(3-chloropropyl)pyrrolidine (10 mg, 0.07 mmol) and a catalytic amount of sodium iodide were added. The reaction was heated at 70° C. for 2.5 hours. Saturated sodium bicarbonate solution was added, and the mixture was extracted with ethyl acetate. The organic extracts were dried over MgSO$_4$, concentrated, and purified by semi-prep LC-MS to give 3.5 mg of the desired product. LC-MS (C$_{20}$H$_{23}$N$_3$O calculated 321) m/z 322 (M+H).

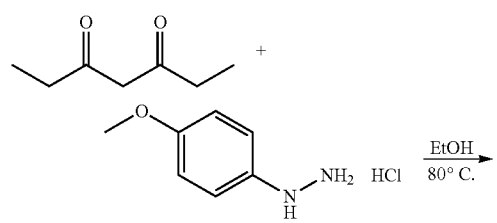

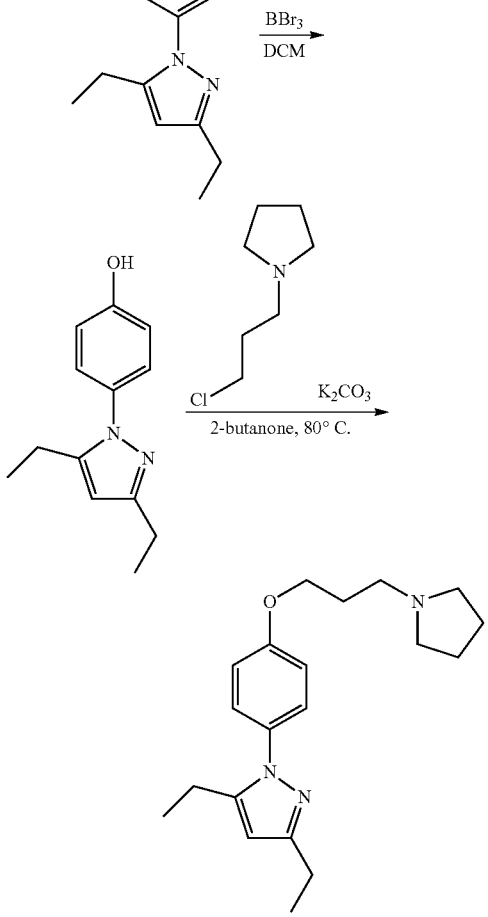

EXAMPLE 21

3,5-Diethyl-1-[4-(3-pyrrolidin-1-ylpropoxy)phenyl]-1H-pyrazole

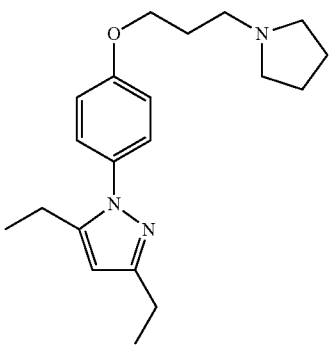

3,5-Diethyl-1-(4-methoxyphenyl)-1H-pyrazole. A solution of 3,5-heptanedione (1.06 mL, 7.80 mmol) and 4-methoxyphenylhydrazine hydrochloride (1.49 g, 8.58 mmol) in ethanol (25 mL) was stirred at 60° C. overnight. After the reaction was concentrated, the residue was partitioned between 1 N HCl and ethyl acetate. The ethyl acetate layer was washed two times with 1 N HCl. The organic layer was dried (MgSO$_4$) and concentrated to give 893 mg of the title compound. LC-MS (C$_{14}$H$_{18}$N$_2$O calculated 230) m/z 231 (M+H).

4-(3,5-Diethylpyrazol-1-yl)phenol. To a solution of 3,5-diethyl-1-(4-methoxyphenyl)-1H-pyrazole (893 mg, 3.88 mmol) in methylene chloride (50 mL) at −78° C. was added boron tribromide (1.10 mL, 11.63 mmol). The reaction was stirred at −78° C. for 1 hour and at room temperature for an additional 1 hour. The reaction was quenched with saturated sodium bicarbonate. After the aqueous layer was extracted with methylene chloride, the combined organic layers were dried (MgSO$_4$) and concentrated to give the desired product. The reaction was assumed to be quantitative. LC-MS (C$_{13}$H$_{16}$N$_2$O calculated 216) m/z 217 (M+H).

3,5-Diethyl-1-[4-(3-pyrrolidin-1-ylpropoxy)phenyl]-1H-pyrazole. To a solution of 4-(3,5-diethylpyrazol-1-yl)phenol (50 mg, 0.23 mmol) in 2-butanone (2 mL) was added potassium carbonate (35 mg, 0.25 mmol) and 1-(3-chloropropyl) pyrrolidine (37 mg, 0.25 mmol). The vial was capped and the reaction was heated overnight at 80° C. After the reaction was diluted with water and extracted with methylene chloride, the organic layer was dried (MgSO$_4$) and concentrated. The residue was purified by semi-prep LC-MS to give 7.0 mg of the desired product. LC-MS (C$_{20}$H$_{29}$N$_3$O calculated 327) m/z 328 (M+H); $^1$H NMR (300 MHz, CDCl$_3$) δ 7.29 (d, J=9.0 Hz, 2H), 6.94 (d, J=8.7 Hz, 2H), 6.02 (s, 1H), 4.05 (t, J=6.3 Hz, 2H), 2.73-2.54 (m, 10H), 2.06 (quint, J=6.3 Hz, 2H), 1.83 (s, 4H), 1.28 (t, J=7.5 Hz, 3H), 1.19 (t, J=7.5 Hz, 3H).

The following compounds were synthesized according to the procedure for Example 21:

| Example | Compound name | MS (ES+) |
|---|---|---|
| 22 | 3,5-Diethyl-1-[4-(3-piperidin-1-ylpropoxy)phenyl]-1H-pyrazole | 342 |
| 23 | 3,5-Diethyl-1-[4-(3-morpholin-1-ylpropoxy)phenyl]-1H-pyrazole | 344 |
| 24 | 3,5-Diisopropyl-1-[4-(3-pyrrolidin-1-yl-propoxy)-phenyl]-1H-pyrazole | 356 |
| 25 | 3,5-Diisopropyl-1-[4-(3-piperidin-1-yl-propoxy)-phenyl]-1H-pyrazole | 370 |
| 26 | 3-tert-Butyl-5-methyl-1-[4-(3-pyrrolidin-1-ylpropoxy)-phenyl]-1H-pyrazole | 342 |
| 27 | 3-tert-Butyl-5-methyl-1-[4-(3-piperidin-1-ylpropoxy)-phenyl]-1H-pyrazole | 356 |
| 28 | 5-Isobutyl-3-methyl-1-[4-(3-pyrrolidin-1-ylpropoxy)-phenyl]-1H-pyrazole | 342 |
| 29 | 5-Isobutyl-3-methyl-1-[4-(3-piperidin-1-ylpropoxy)-phenyl]-1H-pyrazole | 356 |
| 30 | 5-Isobutyl-3-methyl-1-[4-(3-piperidin-1-ylpropoxy)-phenyl]-2H-pyrazole | 356 |
| 31 | 5-Isobutyl-3-methyl-1-[4-(3-pyrrolidin-1-ylpropoxy)-phenyl]-2H-pyrazole | 342 |
| 32 | 1-Cyclobutyl-4-[4-(3,5-diisopropylpyrazol-1-yl)phenoxy]piperidine | 382 |
| 33 | 5-tert-Butyl-3-methyl-1-[4-(3-pyrrolidin-1-ylpropoxy)-phenyl]-1H-pyrazole | 342 |
| 34 | 5-tert-Butyl-3-methyl-1-[4-(3-piperidin-1-ylpropoxy)-phenyl]-1H-pyrazole | 356 |
| 35 | 3,5-Dimethyl-1-[4-(3-pyrrolidin-1-ylpropoxy)phenyl]-1H-pyrazole | 300 |
| 36 | 3,4,5-Trimethyl-1-[4-(3-pyrrolidin-1-ylpropoxy)phenyl]-1H-pyrazole | 314 |
| 37 | 4-Ethyl-3,5-dimethyl-1-[4-(3-pyrrolidin-1-ylpropoxy)phenyl]-1H-pyrazole | 328 |
| 38 | 4-Butyl-3,5-dimethyl-1-[4-(3-pyrrolidin-1-ylpropoxy)phenyl]-1H-pyrazole | 356 |
| 39 | 4-Phenyl-3,5-dimethyl-1-[4-(3-pyrrolidin-1-ylpropoxy)phenyl]-1H-pyrazole | 375 |
| 40 | 5-Methyl-3-phenyl-1-[4-(3-pyrrolidin-1-ylpropoxy)phenyl]-1H-pyrazole | 362 |
| 41 | 5-Methyl-3-phenyl-1-[4-(3-pyrrolidin-1-ylpropoxy)phenyl]-2H-pyrazole | 362 |
| 42 | 3-tert-Butyl-5-phenyl-1-[4-(3-pyrrolidin-1-ylpropoxy)phenyl]-1H-pyrazole | 404 |
| 43 | 3-Phenyl-1-[4-(3-pyrrolidin-1-ylpropoxy)phenyl]-4,5,6,7-tetrahydro-1H-indazole | 362 |
| 44 | 3-Phenyl-1-[4-(3-pyrrolidin-1-ylpropoxy)phenyl]-4,5,6,7-tetrahydro-2H-indazole | 362 |
| 45 | 5-Furan-2-yl-3-methyl-1-[4-(3-pyrrolidin-1-ylpropoxy)phenyl]-1H-pyrazole | 352 |
| 46 | 3-Difluoromethyl-5-furan-2-yl-1-[4-(3-pyrrolidin-1-ylpropoxy)phenyl]-1H-pyrazole | 388 |
| 47 | 3-Trifluoromethyl-5-furan-2-yl-1-[4-(3-pyrrolidin-1-ylpropoxy)phenyl]-1H-pyrazole | 406 |
| 48 | 3-Trifluoromethyl-5-thiophen-2-yl-1-[4-(3-pyrrolidin-1-ylpropoxy)phenyl]-1H-pyrazole | 422 |
| 49 | 3-Difluoromethyl-5-phenyl-1-[4-(3-pyrrolidin-1-ylpropoxy)phenyl]-1H-pyrazole | 398 |
| 50 | 5-Phenyl-1-[4-(3-pyrrolidin-1-yl-propoxy)-phenyl]-3-trifluoromethyl-1H-pyrazole | 416 |
| 51 | 1-{4-[3-(2-(R)-Methyl-pyrrolidin-1-yl)-propoxy]-phenyl}-5-phenyl-3-trifluoromethyl-1H-pyrazole | 430 |
| 52 | Dimethyl-(1-{3-[4-(5-phenyl-3-trifluoromethyl-pyrazol-1-yl)-phenoxy]-propyl}-pyrrolidin-3-yl)-amine | 459 |
| 53 | 4-{3-[4-(5-Phenyl-3-trifluoromethyl-pyrazol-1-yl)-phenoxy]-propyl}-morpholine | 432 |

-continued

| Example | Compound name | MS (ES+) |
|---|---|---|
| 54 | 1-{3-[4-(5-Phenyl-3-trifluoromethyl-pyrazol-1-yl)-phenoxy]-propyl}-piperidine | 430 |
| 55 | 3-Methyl-1-[4-(3-pyrrolidin-1-yl-propoxy)-phenyl]-4,5,6,7-tetrahydro-1H-indazole | 340 |
| 56 | 3-Methyl-2-[4-(3-pyrrolidin-1-yl-propoxy)-phenyl]-4,5,6,7-tetrahydro-2H-indazole | 340 |
| 57 | 3-Methyl-1-[4-(3-pyrrolidin-1-yl-propoxy)-phenyl]-1,4,5,6-tetrahydro-cyclopentapyrazole | 326 |
| 58 | 3-Methyl-2-[4-(3-pyrrolidin-1-yl-propoxy)-phenyl]-2,4,5,6-tetrahydro-cyclopentapyrazole | 326 |
| 59 | 3-Methyl-1-[4-(3-piperidin-1-yl-propoxy)-phenyl]-1,4,5,6-tetrahydro-cyclopentapyrazole | 326 |
| 60 | 3-Methyl-2-[4-(3-piperidin-1-yl-propoxy)-phenyl]-2,4,5,6-tetrahydro-cyclopentapyrazole | 340 |
| 61 | 3,5-Diisopropyl-1-[2-methyl-4-(3-pyrrolidin-1-ylpropoxy)phenyl]-1H-pyrazole | 370 |
| 62 | 3,5-Diisopropyl-1-[2-methyl-4-(3-piperidin-1-ylpropoxy)phenyl]-1H-pyrazole | 384 |
| 63 | 5-Benzofuran-2-yl-1-[4-(3-pyrrolidin-1-ylpropoxy)phenyl]-3-trifluoromethyl-1H-pyrazole | 456 |
| 64 | 3-Methyl-1-[4-(3-pyrrolidin-1-yl-propoxy)-phenyl]-1H-benzo[4,5]thieno[3,2-c]pyrazole | 392 |
| 65 | 3-Methyl-1-{4-[3-(2-methyl-pyrrolidin-1-yl)-propoxy]-phenyl}-1H-benzo[4,5]thieno[3,2-c]pyrazole | 406 |
| 66 | 3-[4-(3-Pyrrolidin-1-yl-propoxy)-phenyl]-1-trifluoromethyl-3H-8-oxa-2,3-diaza-cyclopenta[a]indene | 430 |
| 67 | 3-{4-[3-(2-Methyl-pyrrolidin-1-yl)-propoxy]-phenyl}-1-trifluoromethyl-3H-8-oxa-2,3-diaza-cyclopenta[a]indene | 444 |
| 68 | Dimethyl-(1-{3-[4-(1-trifluoromethyl-8-oxa-2,3-diaza-cyclopenta[a]inden-3-yl)-phenoxy]-propyl}-pyrrolidin-3-yl)-amine | 473 |

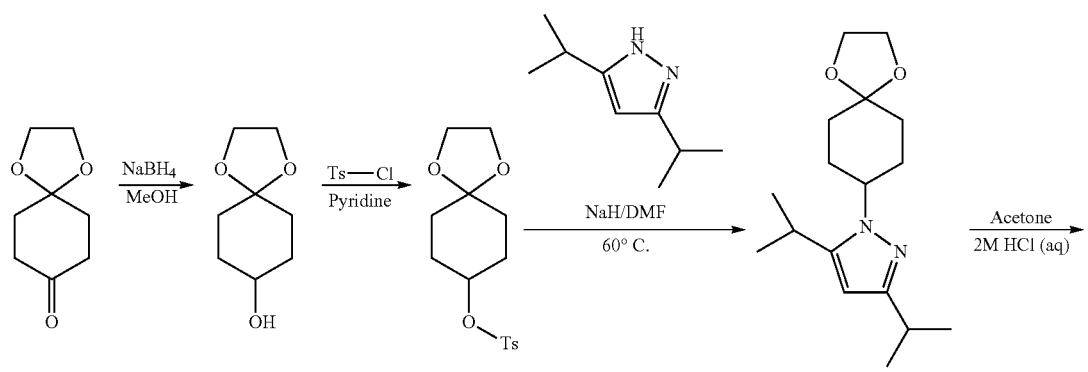

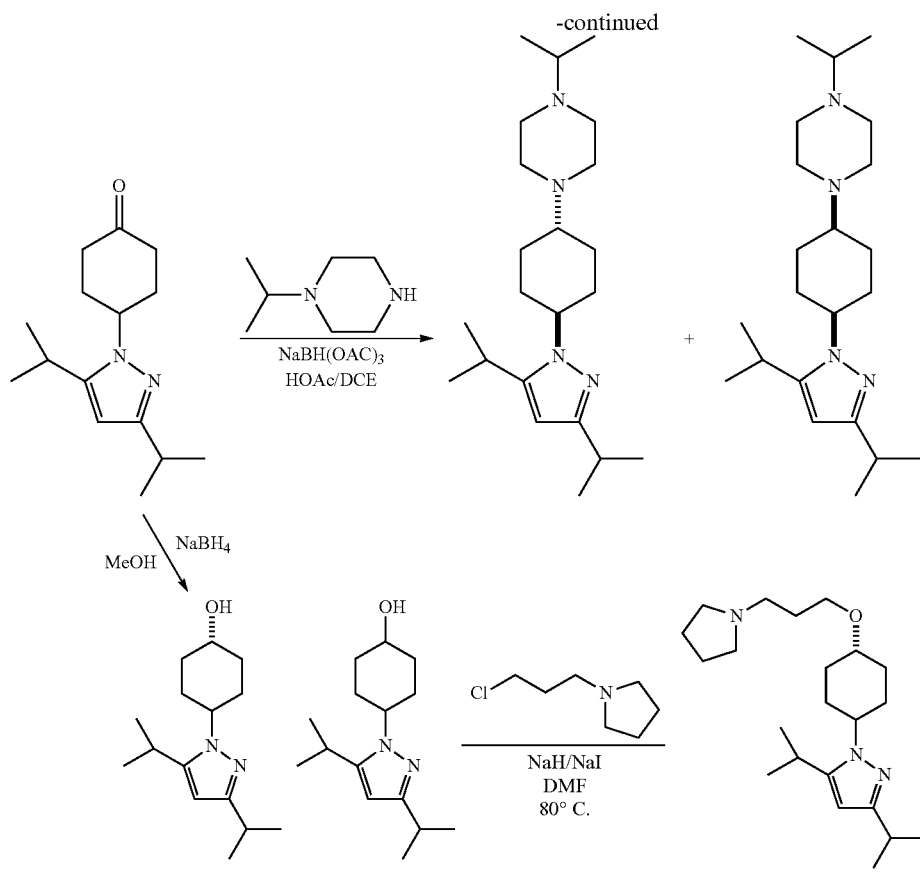

EXAMPLES 69 AND 70

1-[4-trans-(3,5-Diisopropyl-pyrazol-1-yl)-cyclohexyl]-4-isopropyl-piperazine and 1-[4-cis-(3,5-Diisopropyl-pyrazol-1-yl)-cyclohexyl]-4-isopropyl-piperazine

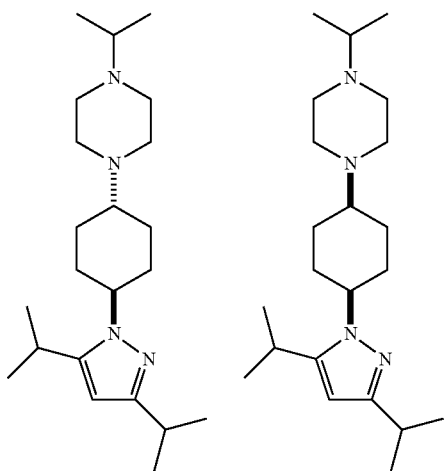

1,4-Dioxa-spiro[4.5]decan-8-ol. To a methanol (50 mL) solution of 1,4-dioxa-spiro[4.5]decan-8-one (5 g, 32 mmol) at 0° C. was added NaBH$_4$ (1.34 g, 35.3 mmol) in 4 portions. The solution was stirred at 0° C. for 15 min followed by stirring at room temperature. for 1 hour. The methanol was evaporated and the residue partitioned between ether and water. The organic layer was separated, dried over Na$_2$SO$_4$ and concentrated to give the desired alcohol as a colorless oil (4.92 g). LC-MS (C$_8$H$_{14}$O$_3$ calculated 158) m/z 159 (M+H); $^1$H NMR (300 MHz, CDCl$_3$) δ 3.90 (s, 4H), 3.77 (m, 1H), 1.82 (m, 4H), 1.55 (m, 4 H).

Toluene-4-sulfonic acid 1,4-dioxa-spiro[4.5]dec-8-yl ester. The alcohol prepared previously, 1,4-dioxa-spiro[4.5] decan-8-ol (4.92 g, 31.1 mmol) was dissolved in pyridine (15 mL) at 0° C. followed by addition of p-toluenesulfonyl chloride (6.1 g, 32.1 mmol). The mixture was stirred at 0° C. for 2 hours and allowed to warm to room temperature overnight. The reaction was diluted with water (15 mL) and stirred for 30 minutes. The reaction was filtered and the precipitate washed with water and recrystallized from hexanes to give the tosylate as an off white solid (yield 7.31 g). LC-MS (C$_{15}$H$_{20}$O$_5$S calculated 312) m/z 313 (M+H).

1-(1,4-Dioxa-spiro[4.5]dec-8-yl)-3,5-diisopropyl-1H-pyrazole. Sodium hydride (66 mg, 60% suspension in oil) was added to a solution of 2,5-diisopropylpyrazole (0.25 g, 1.64 mmol) in dry DMF (5 ml). The solution was stirred at room temperature until hydrogen evolution stopped and the solution cooled on ice for 5 minutes. To the reaction was added a solution of toluene-4-sulfonic acid 1,4-dioxa-spiro[4.5]dec-8-yl ester (0.467 g, 1.5 mmol) in DMF (1 mL) and stirred at 0° C. for 5 minutes. The reaction was then heated to 60° C. overnight. The reaction was cooled, quenched with water and partitioned between ethyl acetate and water. The organic layer was separated, washed with water, dried over Na$_2$SO$_4$ and purified on silica gel (2:1 Hexane:EtOAc) to give the desired product (yield 41 mg). LC-MS (C$_{17}$H$_{28}$N$_2$O$_2$ calculated 292) m/z 293 (M+H).

4-(3,5-Diisopropyl-pyrazol-1-yl)-cyclohexanone. To a solution of 1-(1,4-dioxa-spiro[4.5]dec-8-yl)-3,5-diisopropyl-1H-pyrazole (40 mg) in acetone (20 ml) was added HCl (20 mL, 2M aq). The reaction was heated to reflux overnight. The reaction was cooled, concentrated and extracted with EtOAc. The organic fractions were washed with water, saturated NaHCO$_3$ and dried over Na$_2$SO$_4$. The solution was concentrated and used without further purification (Yield 30.6 mg). LC-MS (C$_{15}$H$_{24}$N$_2$O calculated 248) m/z 249 (M+H).

1-[4-trans-(3,5-Diisopropyl-pyrazol-1-yl)-cyclohexyl]-4-isopropyl-piperazine and 1-[4-cis-(3,5-Diisopropyl-pyrazol-1-yl)-cyclohexyl]-4-isopropyl-piperazine. To a solution of 4-(3,5-diisopropyl-pyrazol-1-yl)-cyclohexanone (30 mg, 0.121 mmol) and 1-isopropylpiperazine (23.3 mg, 26 uL) in dichloroethane (2 mL) was added acetic acid (100 uL). The solution was stirred at room temperature for 2 hours followed by addition of NaBH(OAc)$_3$. The reaction was concentrated under reduced pressure and the products separated by reverse phase HPLC to give 1-[4-cis-(3,5-Diisopropyl-pyrazol-1-yl)-cyclohexyl]-4-isopropyl-piperazine (yield 13.2 mg) and 1-[4-trans-(3,5-Diisopropyl-pyrazol-1-yl)-cyclohexyl]-4-isopropyl-piperazine (yield 6.1 mg). LC-MS (C$_{20}$H$_{40}$N$_4$ calculated 360) m/z 361 (M+H).

EXAMPLES 71 AND 72

3,5-Diisopropyl-1-[trans-4-(3-pyrrolidin-1-yl-propoxy)-cyclohexyl]-1H-pyrazole and 3,5-Diisopropyl-1-[cis-4-(3-pyrrolidin-1-yl-propoxy)-cyclohexyl]-1H-pyrazole

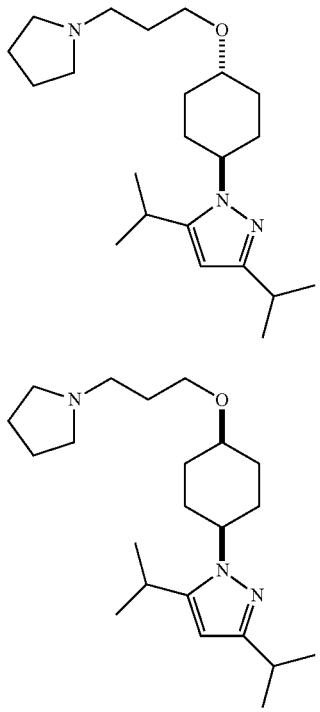

Trans-4-(3,5-diisopropyl-pyrazol-1-yl)-cyclohexanol and cis-4-(3,5-diisopropyl-pyrazol-1-yl)-cyclohexanol. To a solution of 4-(3,5-diisopropyl-pyrazol-1-yl)-cyclohexanone (236 mg, 0.95 mmol) in methanol (10 mL) was added NaBH$_4$ (38 mg, 1 mmol). The reaction was stirred at room temperature overnight followed by acidification with HCl (10% aqueous). The reaction was diluted with EtOAc and extracted with water, brine, dried over MgSO$_4$ and concentrated. The residue was purified on silica gel (100% hexane to 4:1 hexane:EtOAc) to give trans-4-(3,5-diisopropyl-pyrazol-1-yl)-cyclohexanol (yield 43.3 mg) and cis-4-(3,5-diisopropyl-pyrazol-1-yl)-cyclohexanol (yield 121 mg) as colorless solids. LC-MS (C$_{15}$H$_{26}$N$_2$O calculated 250) m/z 251 (M+H).

3,5-Diisopropyl-1-[cis-4-(3-pyrrolidin-1-yl-propoxy)-cyclohexyl]-1H-pyrazole. Cis-4-(3,5-diisopropyl-pyrazol-1-yl)-cyclohexanol (17.5 mg, 0.068 mmol) was dissolved in dry DMF (2 mL) followed by addition of NaH (excess, 60% in oil) and stirred at room temperature until hydrogen evolution stopped. To the reaction was added 1-(3-Chloro-propyl)-pyrrolidine (20 mg) and catalytic NaI followed by heating to 80° C. overnight. The reaction was cooled, quenched with methanol and concentrated under reduced pressure. The residue was purified by prep HPLC to give the desired product (yield 10.6 mg). LC-MS (C$_{22}$H$_{39}$N$_3$O calculated 361) m/z 362 (M+H).

Trans-4-(3,5-diisopropyl-pyrazol-1-yl)-cyclohexanol was prepared by the same method starting with trans-4-(3,5-diisopropyl-pyrazol-1-yl)-cyclohexanol.

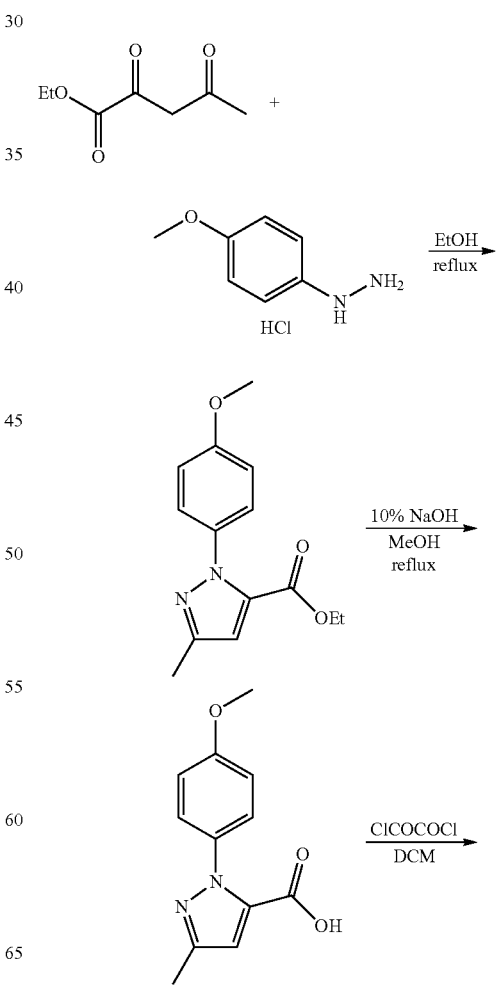

EXAMPLE 73

5-Methyl-2-[4-(3-pyrrolidin-1-yl-propoxy)-phenyl]-2H-pyrazole-3-carboxylic acid cyclohexylamide

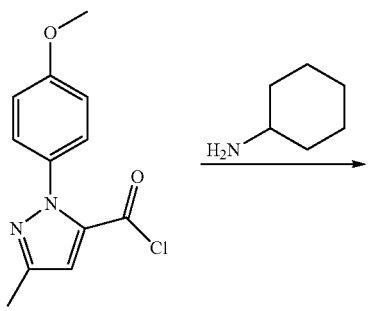
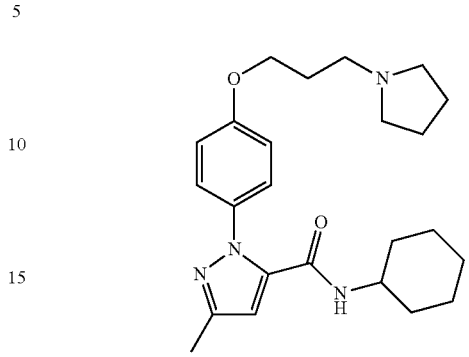
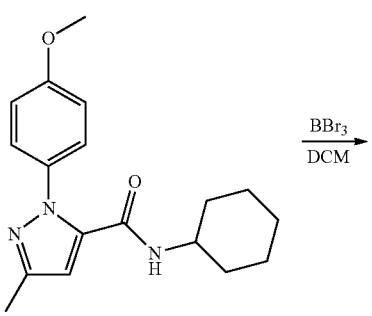
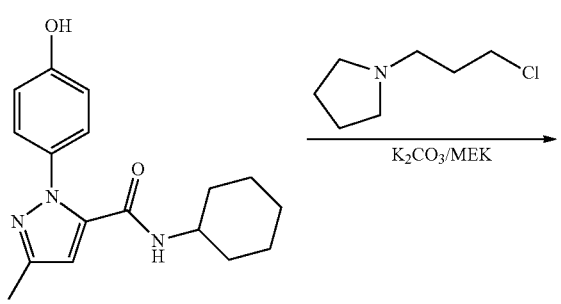
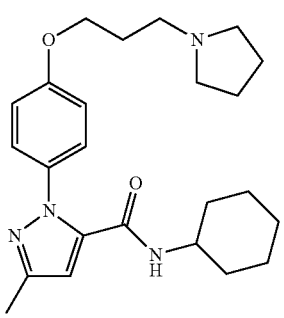

2-(4-Methoxy-phenyl)-5-methyl-2H-pyrazole-3-carboxylic acid ethyl ester. Ethyl-2,4-dioxovalerate (0.555 g, 3.5 mmol) and 4-methoxyphenylhydrazine hydrochloride (0.67 g, 3.8 mmol) were mixed in ethanol and heated to 80° C. overnight. The reaction was cooled, diluted with water and extracted with EtOAc. Organic layers were combined and washed with water, 10% HCl, sat. NaHCO$_3$, dried over MgSO$_4$ and concentrated under reduced pressure. The residue was purified on silica gel (20% EtOAc in hexanes to 30% EtOAc in hexanes). Two regioisomers were isolated, the title regioisomer being the more polar (yield 492 mg). LC-MS (C$_{14}$H$_{16}$N$_2$O$_3$ calculated 260) m/z 261 (M+H).

2-(4-Methoxy-phenyl)-5-methyl-2H-pyrazole-3-carboxylic acid. To a solution of 2-(4-Methoxy-phenyl)-5-methyl-2H-pyrazole-3-carboxylic acid ethyl ester (400 mg) in a 1:1:1 mixture of MeOH:THF:water was added 10% NaOH (20 mL). The mixture was heated to reflux and the reaction monitored by TLC and HPLC until hydrolysis was complete. The solution was cooled and concentrated under reduced pressure. The residue was acidified with 10% HCl and extracted with EtOAc. The organic fractions were combined and dried over MgSO$_4$ and concentrated under reduced pressure. The resulting solid was used without further purification (Yield 242 mg). LC-MS (C$_{12}$H$_{12}$N$_2$O$_3$ calculated 232) m/z 231 (M−H).

2-(4-Methoxy-phenyl)-5-methyl-2H-pyrazole-3-carboxylic acid cyclohexyl amide. The acid prepared above, 2-(4-Methoxy-phenyl)-5-methyl-2H-pyrazole-3-carboxylic acid (234 mg, 1 mmol) was suspended in DCM (8 mL). To this suspension was added oxalyl chloride (115 uL, 166 mg, 1.3 mmol) followed by one drop of DMSO. The reaction was stirred at room temperature for 1 hour. The reaction was concentrated to dryness, diluted with DCM (20 mL) and concentrated under reduced pressure a second time to ensure removal of any excess oxalyl chloride. The intermediate acid chloride was dissolved in DCM (15 mL) followed by drop wise addition of cyclohexylamine (0.22 g, 2.2 mmol) at room temperature. for 1 hour. The reaction was diluted with DCM and extracted with water, 10% NaOH, 10% HCl and dried over Na$_2$SO$_4$. The solvent was removed and the product used without further purification (Yield 0.167 g). LC-MS (C$_{18}$H$_{23}$N$_4$O$_2$ calculated 313) m/z 314 (M+H).

2-(4-Methoxy-phenyl)-5-methyl-2H-pyrazole-3-carboxylic acid cyclohexyl amide was converted into the final product by the method described in Example 21

The following compounds were synthesized according to the procedure for Example 73:

| Example | Compound name | MS (ES+) |
|---|---|---|
| 74 | 5-Methyl-2-{4-[3-(2R-methylpyrrolidin-1-yl)propoxy]phenyl}-2H-pyrazole-3-carboxylic acid cyclohexylamide | 425 |
| 75 | 5-Methyl-2-[4-(3-piperidin-1-ylpropoxy)phenyl]-2H-pyrazole-3-carboxylic acid cyclohexylamide | 425 |
| 76 | 5-Methyl-2-[4-(3-morpholin-4-ylpropoxy)phenyl]-2H-pyrazole-3-carboxylic acid cyclohexylamide | 427 |
| 77 | 5-Methyl-2-{4-[2-(1-methylpyrrolidin-2-yl)ethoxy]phenyl}-2H-pyrazole-3-carboxylic acid cyclohexylamide | 411 |
| 78 | {5-Methyl-2-[4-(3-pyrrolidin-1-ylpropoxy)phenyl]-2H-pyrazol-3-yl}pyrrolidin-1-ylmethanone | 383 |
| 79 | 5-Methyl-2-[4-(3-pyrrolidin-1-ylpropoxy)phenyl]-2H-pyrazole-3-carboxylic acid cyclohexylmethylamide | 425 |
| 80 | 5-Methyl-2-[4-(3-pyrrolidin-1-ylpropoxy)phenyl]-2H-pyrazole-3-carboxylic acid cyclobutylamide | 383 |
| 81 | 5-Methyl-2-[4-(3-pyrrolidin-1-ylpropoxy)phenyl]-2H-pyrazole-3-carboxylic acid phenylamide | 405 |
| 82 | 5-Methyl-2-[4-(octahydroquinolizin-1-ylmethoxy)phenyl]-2H-pyrazole-3-carboxylic acid cyclohexylamide | 451 |
| 83 | 5-Methyl-1-[4-(3-pyrrolidin-1-ylpropoxy)phenyl]-1H-pyrazole-3-carboxylic acid cyclohexylamide | 411 |

Representative compounds of the present invention that were prepared by the procedures of Examples 1-83 were evaluated in binding assays against cells expressing human $H_3$ receptor by the following procedure.

Cell Culture

Materials

[$^{125}$I]iodoproxyfan (2000 Ci/mmol) was obtained from Amersham Bioscience (Piscataway, N.J.). All other chemicals were either from Sigma-Aldrich (St. Louis, Mo.) or Tocris Cookson Inc. (Ellisville, Mo.).

RAGE Methodology

The human histamine H3 receptor was stably expressed in HT1080 cells containing the chimeric G-protein, Gqαi5 (Coward et al., *Anal Biochem* 1999; 270:242-8). HT1080-Gqαi5 cells were grown in alpha-modified MEM containing 10% fetal bovine serum and 7 µg/ml blasticidin at 37° C. in 5% $CO_2$/95% atmosphere. Cells (4.8×10$^9$) were irradiated with 50 rads from a $^{137}$Cs source and the pFG8-HH3 RAGE (Random Activation of Gene Expression; see Harrington et al., *Nature Biotechnology*. 2001; 19:440-45) vector was subsequently integrated into the cells via electroporation (250V, 600 µF, 50Ω). The RAGE vector pFG8-HH3 contained cDNA sequence coding for the first exon (83 amino acids) of human H3 receptor. After electroporation, cells were plated in T75 flasks and grown in alpha-modified MEM. The culture medium was replaced 48 hrs after electroporation with alpha-modified MEM, 10% fetal bovine serum, 500 µg/ml hygromycin B and 3 µg/ml puromycin. Medium was replaced every four days during cell expansion. To identify RAGE activated cells expressing the H3 receptor, pools of approximately 10,000 colonies (5×10$^7$-1.5×10$^8$ cells total) were screened by PCR for the desired gene product (using primers specific to the RAGE vector and exon 2 of the H3 receptor). Pools that were found to contain the appropriate transcript, as confirmed by sequencing, were subcloned into pools of 100 cells/well. Positive 100 cells/well pools were identified by PCR, confirmed by sequencing, and subsequently subcloned to 0.8 cells/well. Once clones expressing the H3 receptor were identified by PCR analysis, assays (FLIPR or radioligand binding) were performed to confirm that the activated gene produced functional protein. The protein expression in the initial clones obtained from the RAGE library was increased by growth in the presence of methotrexate. Since the integrated RAGE vector contains the DHFR gene, such treatment selects for cells that have amplified the genetic locus containing the RAGE insert. Subclones obtained after methotrexate amplification were tested for functional activity in FLIPR assays to identify the clone that was most suitable for HTS. The final HT1080-Gqαi5 RAGE clone (RAGE-H3) expressing the human histamine H3 receptor was grown in alpha-modified MEM containing 10% fetal bovine serum, 3 µg/ml puromycin, 500 µg/ml hygromycin B, 3.2 µM methotrexate at 37° C. in 5% $CO_2$/95% atmosphere.

Membrane Preparation

RAGE-H3 cells (10$^9$) were washed twice with cold PBS, scraped off the plates, and centrifuged at 1000×g for 5 minutes. Cells were resuspended in ice-cold 10 mM Tris HCl, pH 7.4, containing 5 mM EDTA and protease inhibitor cocktail tablets (Roche Molecular Biochemicals). After incubating on ice for 10 min, the cells were homogenized with a dounce homogenizer or a polytron tissue grinder, and centrifuged at 1000×g for 10 min at 4° C. The resulting supernatant was centrifuged at 32,000×g for 30 min at 4° C. The membrane pellets were resuspended in 50 mM Tris HCl, pH 7.4, and stored at −80° C. until use. Protein concentration was determined by the Bradford method (Bio-Rad Laboratories, CA).

Radioligand Binding Assays

Binding assays were carried out in 96-well polypropylene plates in 50 mM Tris HCl, pH 7.4, containing 1 mM EDTA. Reaction mixtures contained 100 µl of membrane suspension, 50 µl of 4% DMSO, and 50 µl of increasing amounts of [$^{125}$I]iodoproxyfan (final concentration 0.0005-1.8 nM for human H3 receptor saturation binding assay). Nonspecific binding was defined by adding 10 µM clobenpropit to the reaction mixtures. Competition binding assays were performed in a reaction mixture containing 100 µl of membrane suspension (~20 µg of protein/well), 50 µl of [$^{125}$I]iodoproxyfan (final concentration of ~0.15 nM) and 50 µl of test compound. Compounds were dissolved in DMSO and then diluted with 4% DMSO; the final maximal DMSO concentration in the binding assays was 1%. Incubations were performed for 1.5 hrs at room temperature and reactions were terminated by rapid filtration over glass fiber GF/C filters (Perkin Elmer, Mass.) using a Brandel cell harvester. The filters were presoaked in 0.3% polyethyleneimine for 30 minutes and were washed with 500 ml of ice-cold 50 mM Tris HCl, pH 7.4. The filters were dried, impregnated with Meltilex wax scintillate (Perkin Elmer, Mass.) and counted with a Betaplate scintillation counter (Perkin Elmer, Mass.).

Data Analysis

All data were analyzed by nonlinear least squares curve fitting using Prism 4.0 software. The $K_D$ and $B_{max}$ for [$^{125}$I] iodoproxyfan were derived from the equation $RL=R_tL/(K_D+L)$, where RL is concentration of receptor-bound ligand at equilibrium, L is the free ligand concentration, and $R_t$ is the total receptor concentration (i.e., $B_{max}$). For competition binding experiments, $IC_{50}$ values (the concentration of compound producing 50% inhibition of specific binding) and Hill Coefficients (nH) were derived from fitting the data to a 4-parameter logistic equation. Apparent $K_i$ values were calculated using the Cheng-Prussof equation of $K_i=IC_{50}/(1+(L/K_D))$, where L is the ligand concentration.

SELECTED EXAMPLES

| Example | Chemical Name | Human H3 (μM) |
|---|---|---|
| 1 | 3-Methyl-1-[4-(3-pyrrolidin-1-ylpropoxy)phenyl]-4,5-dihydro-1H-benzo[g]indazole | <0.01 |
| 2 | 3-Methyl-1-{4-[3-(2R-methylpyrrolidin-1-yl)propoxy]phenyl}-4,5-dihydro-1H-benzo[g]indazole | <0.01 |
| 3 | 3-Methyl-1-[4-(3-morpholin-4-ylpropoxy)phenyl]-4,5-dihydro-1H-benzo[g]indazole | <0.01 |
| 4 | 1-[4-(3-Pyrrolidin-1-ylpropoxy)phenyl]-5-styryl-3-trifluoromethyl-1H-pyrazole | <0.1 |
| 5 | 3-Methyl-2-[4-(3-pyrrolidin-1-ylpropoxy)phenyl]-4,5,5a,6,7,8,9,9a-octahydro-1H-benzo[g]indazole | <0.001 |
| 6 | 3-Methyl-2-[4-(3-pyrrolidin-1-ylpropoxy)phenyl]-4,5,5a,6,7,8,9,9a-octahydro-2H-benzo[g]indazole | <0.01 |
| 7 | 8-Methoxy-3-methyl-1-[4-(3-pyrrolidin-1-ylpropoxy)phenyl]-4,5-dihydro-1H-benzo[g]indazole | <0.1 |
| 8 | 6-Methoxy-3-methyl-1-[4-(3-pyrrolidin-1-ylpropoxy)phenyl]-4,5-dihydro-1H-benzo[g]indazole | <0.01 |
| 9 | 7-Methoxy-3-methyl-1-[4-(3-pyrrolidin-1-ylpropoxy)phenyl]-4,5-dihydro-1H-benzo[g]indazole | <0.1 |
| 10 | 2-[4-(1-Cyclopentylpiperidin-4-yloxy)phenyl]-5-methyl-2H-pyrazole-3-carboxylic acid cyclohexylamide | <0.01 |
| 11 | 2-[4-(1-Cyclohexylpiperidin-4-yloxy)phenyl]-5-methyl-2H-pyrazole-3-carboxylic acid cyclohexylamide | <0.01 |
| 12 | 2-[4-(1-Isopropylpiperidin-4-yloxy)phenyl]-5-methyl-2H-pyrazole-3-carboxylic acid cyclohexylamide | <0.01 |
| 13 | 2-[4-(1-Cyclobutylpiperidin-4-yloxy)phenyl]-5-methyl-2H-pyrazole-3-carboxylic acid cyclohexylamide | <0.01 |
| 14 | {5-Methyl-2-[4-(3-pyrrolidin-1-ylpropoxy)phenyl]-2H-pyrazol-3-yl}methanol | <0.01 |
| 15 | 5-Cyclopentyloxymethyl-3-methyl-1-[4-(3-pyrrolidin-1-ylpropoxy)-phenyl]-1H-pyrazole | <0.01 |
| 16 | 5-Cyclohexyloxymethyl-3-methyl-1-[4-(3-pyrrolidin-1-ylpropoxy)phenyl]-1H-pyrazole | <0.01 |
| 17 | 5-Isopropoxymethyl-3-methyl-1-[4-(3-pyrrolidin-1-ylpropoxy)-phenyl]-1H-pyrazole | <0.1 |
| 18 | 1-[4-(3-Pyrrolidin-1-ylpropoxy)phenyl]-2H-indazole | <0.1 |
| 19 | 4-(4-Methoxyphenyl)-3,5-dimethyl-1-[4-(3-pyrrolidin-1-ylpropoxy)phenyl]-1H-pyrazole | <0.01 |
| 20 | 1-[4-(3-Pyrrolidin-1-ylpropoxy)phenyl]-1H-indazole | <0.01 |
| 21 | 3,5-Diethyl-1-[4-(3-pyrrolidin-1-ylpropoxy)phenyl]-1H-pyrazole | <0.01 |
| 22 | 3,5-Diethyl-1-[4-(3-piperidin-1-ylpropoxy)phenyl]-1H-pyrazole | <0.01 |
| 23 | 3,5-Diethyl-1-[4-(3-morpholin-1-ylpropoxy)phenyl]-1H-pyrazole | <1 |
| 24 | 3,5-Diisopropyl-1-[4-(3-pyrrolidin-1-yl-propoxy)-phenyl]-1H-pyrazole | <0.01 |
| 25 | 3,5-Diisopropyl-1-[4-(3-piperidin-1-yl-propoxy)-phenyl]-1H-pyrazole | <0.01 |
| 26 | 3-tert-Butyl-5-methyl-1-[4-(3-pyrrolidin-1-ylpropoxy)-phenyl]-1H-pyrazole | <0.01 |
| 27 | 3-tert-Butyl-5-methyl-1-[4-(3-piperidin-1-ylpropoxy)-phenyl]-1H-pyrazole | <0.01 |
| 28 | 5-Isobutyl-3-methyl-1-[4-(3-pyrrolidin-1-ylpropoxy)-phenyl]-1H-pyrazole | <0.1 |
| 29 | 5-Isobutyl-3-methyl-1-[4-(3-piperidin-1-ylpropoxy)-phenyl]-1H-pyrazole | <0.1 |
| 30 | 5-Isobutyl-3-methyl-1-[4-(3-piperidin-1-ylpropoxy)-phenyl]-2H-pyrazole | <0.01 |
| 31 | 5-Isobutyl-3-methyl-1-[4-(3-pyrrolidin-1-ylpropoxy)-phenyl]-2H-pyrazole | <0.01 |
| 32 | 1-Cyclobutyl-4-[4-(3,5-diisopropylpyrazol-1-yl)phenoxy]piperidine | <0.01 |
| 33 | 5-tert-Butyl-3-methyl-1-[4-(3-pyrrolidin-1-ylpropoxy)-phenyl]-1H-pyrazole | <0.01 |
| 34 | 5-tert-Butyl-3-methyl-1-[4-(3-piperidin-1-ylpropoxy)-phenyl]-1H-pyrazole | <0.1 |
| 35 | 3,5-Dimethyl-1-[4-(3-pyrrolidin-1-ylpropoxy)phenyl]-1H-pyrazole | <0.01 |
| 36 | 3,4,5-Trimethyl-1-[4-(3-pyrrolidin-1-ylpropoxy)phenyl]-1H-pyrazole | <0.01 |
| 37 | 4-Ethyl-3,5-dimethyl-1-[4-(3-pyrrolidin-1-ylpropoxy)phenyl]-1H-pyrazole | <0.01 |
| 38 | 4-Butyl-3,5-dimethyl-1-[4-(3-pyrrolidin-1-ylpropoxy)phenyl]-1H-pyrazole | <0.01 |
| 39 | 4-Phenyl-3,5-dimethyl-1-[4-(3-pyrrolidin-1-ylpropoxy)phenyl]-1H-pyrazole | <0.01 |
| 40 | 5-Methyl-3-phenyl-1-[4-(3-pyrrolidin-1-ylpropoxy)phenyl]-1H-pyrazole | <0.01 |
| 41 | 5-Methyl-3-phenyl-1-[4-(3-pyrrolidin-1-ylpropoxy)phenyl]-2H-pyrazole | <0.01 |
| 42 | 3-tert-Butyl-5-phenyl-1-[4-(3-pyrrolidin-1-ylpropoxy)phenyl]-1H-pyrazole | <0.01 |
| 43 | 3-Phenyl-1-[4-(3-pyrrolidin-1-ylpropoxy)phenyl]-4,5,6,7-tetrahydro-1H-indazole | <1 |
| 44 | 3-Phenyl-1-[4-(3-pyrrolidin-1-ylpropoxy)phenyl]-4,5,6,7-tetrahydro-2H-indazole | <0.1 |
| 44 | 5-Furan-2-yl-3-methyl-1-[4-(3-pyrrolidin-1-ylpropoxy)phenyl]-1H-pyrazole | <0.01 |
| 45 | 3-Difluoromethyl-5-furan-2-yl-1-[4-(3-pyrrolidin-1-ylpropoxy)phenyl]-1H-pyrazole | <0.01 |
| 46 | 5-Furan-2-yl-1-[4-(3-pyrrolidin-1-ylpropoxy)phenyl]-3-trifluoromethyl-1H-pyrazole | <0.01 |
| 47 | 1-[4-(3-Pyrrolidin-1-ylpropoxy)phenyl]-5-thiophen-2-yl-3-trifluoromethyl-1H-pyrazole | <0.01 |
| 48 | 3-Difluoromethyl-5-phenyl-1-[4-(3-pyrrolidin-1-ylpropoxy)phenyl]-1H-pyrazole | <0.01 |
| 50 | 5-Phenyl-1-[4-(3-pyrrolidin-1-ylpropoxy)phenyl]-3-trifluoromethyl-1H-pyrazole | <0.01 |
| 51 | 1-{4-[3-(2R-Methylpyrrolidin-1-yl)propoxy]phenyl}-5-phenyl-3-trifluoromethyl-1H-pyrazole | <0.1 |

-continued

| Example | Chemical Name | Human H3 (μM) |
|---|---|---|
| 52 | Dimethyl(1-{3-[4-(5-phenyl-3-trifluoromethylpyrazol-1-yl)phenoxy]propyl}pyrrolidin-3-yl)amine | <10 |
| 53 | 4-{3-[4-(5-Phenyl-3-trifluoromethylpyrazol-1-yl)phenoxy]propyl}morpholine | <1 |
| 54 | 1-{3-[4-(5-Phenyl-3-trifluoromethylpyrazol-1-yl)phenoxy]propyl}piperidine | <0.1 |
| 55 | 3-Methyl-1-[4-(3-pyrrolidin-1-ylpropoxy)-phenyl]-4,5,6,7-tetrahydro-1H-indazole | <0.01 |
| 56 | 3-Methyl-1-[4-(3-pyrrolidin-1-ylpropoxy)-phenyl]-4,5,6,7-tetrahydro-2H-indazole | <0.001 |
| 57 | 3-Methyl-1-[4-(3-pyrrolidin-1-ylpropoxy)phenyl]-1,4,5,6-tetrahydrocyclopentapyrazole | <0.01 |
| 58 | 3-Methyl-2-[4-(3-pyrrolidin-1-ylpropoxy)phenyl]-2,4,5,6-tetrahydrocyclopentapyrazole | <0.1 |
| 59 | 3-Methyl-1-[4-(3-piperidin-1-ylpropoxy)phenyl]-1,4,5,6-tetrahydrocyclopentapyrazole | <0.01 |
| 60 | 3-Methyl-2-[4-(3-piperidin-1-ylpropoxy)phenyl]-2,4,5,6-tetrahydrocyclopentapyrazole | <0.01 |
| 61 | 3,5-Diisopropyl-1-[2-methyl-4-(3-pyrrolidin-1-ylpropoxy)phenyl]-1H-pyrazole | <0.01 |
| 62 | 3,5-Diisopropyl-1-[2-methyl-4-(3-piperidin-1-ylpropoxy)phenyl]-1H-pyrazole | <0.01 |
| 63 | 5-Benzofuran-2-yl-1-[4-(3-pyrrolidin-1-ylpropoxy)phenyl]-3-trifluoromethyl-1H-pyrazole | <0.1 |
| 64 | 3-Methyl-1-[4-(3-pyrrolidin-1-yl-propoxy)-phenyl]-1H-benzo[4,5]thieno[3,2-c]pyrazole | <0.01 |
| 65 | 3-Methyl-1-{4-[3-(2-methyl-pyrrolidin-1-yl)-propoxy]-phenyl}-1H-benzo[4,5]thieno[3,2-c]pyrazole | <0.01 |
| 66 | 3-[4-(3-Pyrrolidin-1-yl-propoxy)-phenyl]-1-trifluoromethyl-3H-8-oxa-2,3-diaza-cyclopenta[a]indene | <1 |
| 67 | 3-{4-[3-(2-Methyl-pyrrolidin-1-yl)-propoxy]-phenyl}-1-trifluoromethyl-3H-8-oxa-2,3-diaza-cyclopenta[a]indene | <0.1 |
| 68 | Dimethyl-(1-{3-[4-(1-trifluoromethyl-8-oxa-2,3-diaza-cyclopenta[a]inden-3-yl)-phenoxy]-propyl}-pyrrolidin-3-yl)-amine | <1 |
| 73 | 5-Methyl-2-[4-(3-pyrrolidin-1-ylpropoxy)phenyl]-2H-pyrazole-3-carboxylic acid cyclohexylamide | <0.001 |
| 74 | 5-Methyl-2-{4-[3-(2R-methylpyrrolidin-1-yl)propoxy]phenyl}-2H-pyrazole-3-carboxylic acid cyclohexylamide | <0.001 |
| 75 | 5-Methyl-2-[4-(3-piperidin-1-ylpropoxy)phenyl]-2H-pyrazole-3-carboxylic acid cyclohexylamide | <0.001 |
| 76 | 5-Methyl-2-[4-(3-morpholin-4-ylpropoxy)phenyl]-2H-pyrazole-3-carboxylic acid cyclohexylamide | <0.01 |
| 77 | 5-Methyl-2-{4-[2-(1-methylpyrrolidin-2-yl)ethoxy]phenyl}-2H-pyrazole-3-carboxylic acid cyclohexylamide | <1 |
| 78 | {5-Methyl-2-[4-(3-pyrrolidin-1-ylpropoxy)phenyl]-2H-pyrazol-3-yl}pyrrolidin-1-ylmethanone | <0.01 |
| 79 | 5-Methyl-2-[4-(3-pyrrolidin-1-ylpropoxy)phenyl]-2H-pyrazole-3-carboxylic acid cyclohexylmethylamide | <0.001 |
| 80 | 5-Methyl-2-[4-(3-pyrrolidin-1-ylpropoxy)phenyl]-2H-pyrazole-3-carboxylic acid cyclobutylamide | <0.001 |
| 81 | 5-Methyl-2-[4-(3-pyrrolidin-1-ylpropoxy)phenyl]-2H-pyrazole-3-carboxylic acid phenylamide | <0.001 |
| 82 | 5-Methyl-2-[4-(octahydroquinolizin-1-ylmethoxy)phenyl]-2H-pyrazole-3-carboxylic acid cyclohexylamide | >10 |
| 83 | 5-Methyl-1-[4-(3-pyrrolidin-1-ylpropoxy)phenyl]-1H-pyrazole-3-carboxylic acid cyclohexylamide | <0.01 |

What is claimed is:

1. A compound of the formula:

[Structural formula showing a cyclohexyl ring with X—(CH₂)ᵧ—N(R₁)(R₂) substituent, R₃ substituent, and attached to a pyrazole ring bearing R₄, R₅, R₆]

where
X is $NR_7$;
y is 0, 1 or 2;
n is 0 or 1;
q is 0, 1, or 2;
$R_1$ is selected from the group consisting of ($C_1$-$C_5$)alkyl and ($C_3$-$C_6$)cycloalkyl;
$R_3$ is 0-2 of groups selected from halogen, ($C_1$-$C_8$)alkyl, ($C_1$-$C_8$)alkoxy, ($C_3$-$C_7$)cycloalkyl, ($C_3$-$C_7$)cycloalkyl-($C_1$-$C_6$)alkyl, heterocycloalkyl containing 1-3 hetero atoms selected from O and S, and ($C_1$-$C_5$)alkyl-O—($C_1$-$C_5$)alkyl;
$R_4$ and $R_6$ are independently selected from ($C_1$-$C_8$)alkyl, ($C_1$-$C_8$)alkoxy, ($C_3$-$C_7$)cycloalkyl, ($C_3$-$C_7$)cycloalkyl-($C_1$-$C_6$)alkyl, heterocycloalkyl containing 1-3 hetero atoms selected from O, S, and NH, ($C_1$-$C_5$)alkyl-O—($C_1$-$C_5$)alkyl, amide, ($C_1$-$C_5$)alkyl-aryl, and $CF_3$;
$R_5$ is selected from the group consisting of hydrogen, ($C_1$-$C_8$)alkyl, aryl, ($C_1$-$C_5$)alkyl-O—($C_1$-$C_5$)alkyl, and ($C_1$-$C_5$)alkyl-aryl;
or
$R_5$ and $R_4$ and the atoms to which they are attached form a fused 5-6 member saturated carbocyclic ring or a fused 10 member bi-cyclic ring system;
or
$R_5$ and $R_6$ and the atoms to which they are attached form a fused 5-6 member saturated carbocyclic ring or a fused 10 member bi-cyclic ring system;
or
$R_5$ and $R_4$ and the atoms to which they are attached form a fused 5-6 member saturated carbocyclic ring to which a 6 member aromatic ring is fused;
or
$R_5$ and $R_6$ and the atoms to which they are attached form a fused 5-6 member saturated carbocyclic ring to which a 6 member aromatic ring is fused;
or
$R_5$ and $R_6$ and the atoms to which they are attached form a fused benzothiophene or fused benzofuran ring system;

$R_7$ and $R_2$ taken together are —($CH_2CH_2$)— to form a two nitrogen containing ring where y is 0 or 1, or a pharmaceutically acceptable salt thereof.

2. A compound of claim 1 selected from the group consisting of:
- 1-[4-trans-(3,5-Diisopropyl-pyrazol-1-yl)-cyclohexyl]-4-isopropyl-piperazine and
- 1-[4-cis-(3,5-Diisopropyl-pyrazol-1-yl)-cyclohexyl]-4-isopropyl-piperazine.

3. A pharmaceutical composition comprising at least one compound of claim 1 in combination with a pharmaceutically acceptable carrier.

4. A pharmaceutical composition comprising at least one compound of claim 2 in combination with a pharmaceutically acceptable carrier.

* * * * *